US008623368B2

(12) United States Patent
Lee et al.

(10) Patent No.: US 8,623,368 B2
(45) Date of Patent: Jan. 7, 2014

(54) HUMAN RECOMBINANT MONOCLONAL ANTIBODY THAT SPECIFICALLY BINDS TO VCAM-1 AND INHIBITS ADHESION AND TRANSMIGRATION BETWEEN LEUKOCYTES AND ENDOTHELIAL CELLS

(75) Inventors: Jung Tae Lee, Daejeon (KR); Kyung Duk Moon, Daejeon (KR); Ji Yong Yoon, Daejeon (KR); Byung Je Sung, Daejeon (KR); Dong Heon Lee, Daejeon (KR); Dong Eun Lee, Busan (KR); Su Yeon Ryu, Daejeon (KR); Hyun Bo Shim, Seoul (KR); Kyung Jae Kang, Seoul (KR)

(73) Assignee: Hanwha Chemical Corporation (KR)

( * ) Notice: Subject to any disclaimer, the term of this patent is extended or adjusted under 35 U.S.C. 154(b) by 0 days.

(21) Appl. No.: 13/503,103

(22) PCT Filed: Oct. 22, 2010

(86) PCT No.: PCT/KR2010/007303
§ 371 (c)(1),
(2), (4) Date: Apr. 20, 2012

(87) PCT Pub. No.: WO2011/049412
PCT Pub. Date: Apr. 28, 2011

(65) Prior Publication Data
US 2012/0276091 A1    Nov. 1, 2012

(30) Foreign Application Priority Data

Oct. 23, 2009   (KR) .................. 10-2009-0101254
Oct. 22, 2010   (KR) .................. 10-2010-0103523

(51) Int. Cl.
*A61K 39/395*    (2006.01)
*C07K 16/28*    (2006.01)
*G01N 33/53*    (2006.01)

(52) U.S. Cl.
USPC .................. 424/152.1; 424/130.1; 424/133.1; 424/141.1; 424/142.1; 424/143.1; 435/7.1; 435/7.2; 435/7.21; 530/387.1; 530/387.3; 530/388.1; 530/388.15; 530/388.2

(58) Field of Classification Search
None
See application file for complete search history.

(56) References Cited

U.S. PATENT DOCUMENTS

| 5,596,090 | A | 1/1997 | Hoke |
| 6,939,545 | B2 | 9/2005 | Jacobs |
| 7,157,086 | B2 | 1/2007 | Lobb |
| 2007/0280941 | A1* | 12/2007 | Chung et al. ............... 424/143.1 |
| 2010/0183599 | A1* | 7/2010 | Mundy et al. .............. 424/133.1 |
| 2012/0308574 | A1* | 12/2012 | Lee et al. ................... 424/142.1 |

FOREIGN PATENT DOCUMENTS

| KR | 1020070115761 A | 12/2007 |
| WO | WO2007/139359 A | 12/2007 |

OTHER PUBLICATIONS

English Translation of Written Opinion of the International Search Authority for corresponding PCT/KR2010/007303 (May 4, 2012).*
Written Opinion of the International Search Authority for corresponding PCT/KR2010/007303 (Mar. 31, 2012).*
Wang et al., "The crystal structure of an N-terminal two-domain fragment of vascular cell adhesion molecule 1 (VCAM-1): A cyclic peptide based on the domain 1 C-D loop can inhibit VCAM-1-a4 integrin interaction", Proc. Natl. Acad. Sci., Jun. 1995, 92: p. 5714-5718.
Chuluyan et al., "Domains 1 and 4 of Vascular Cell Adhesion Molecule-1 (CD106) Both Support Very late Activation Antigen-4 (CD49d/ CD29)-Dependent Monocyte Transendothelial Migration", The Journal of Immunology, 1995, 155: p. 3135-3144.
International Search Report and Written Opinion from PCT/KR2010/007303, dated Jun. 23, 2011.

* cited by examiner

*Primary Examiner* — Phillip Gambel
(74) *Attorney, Agent, or Firm* — Lathrop & Gage LLP; Brian C. Trinque; Andrew T. Wilkins

(57) ABSTRACT

The present invention relates to a human recombinant monoclonal antibody that specifically binds to human Vascular Cell Adhesion Molecule-1 (VCAM-1) to inhibit adhesion between leukocytes and activated endothelial cells and transmigration of leukocytes through the activated endothelial cells, and a prophylactic and therapeutic composition for inflammatory disease or cancer comprising the same. The human recombinant monoclonal antibody according to the present invention shows a strong affinity to VCAM-1 expressed on human endothelial cell, and effectively inhibits VCAM-1-mediated adhesion between leukocytes and activated endothelial cells and transmigration of leukocytes through the activated endothelial cells, thereby being used for the prevention and treatment of inflammatory disease such as asthma and arthritis, transplant rejection, cardiovascular disease, and cancer.

23 Claims, 17 Drawing Sheets

Fig. 1

VH sequence

| name of clone | Frame 1 | CDR1 | Frame 2 | CDR2 | Frame 3 | CDR3 | Frame 4 |
|---|---|---|---|---|---|---|---|
| H6 (SEQ ID NO. 1) | EVQLLESGGGLVQPG GSLRLSCAASGFTF | SSYDMS (SEQ ID NO. 2) | WVRQAPGKGLE WVS | GISYSGGSTYYA DSVKG (SEQ ID NO. 3) | RFTISRDNSKNTL YLQMNSLRAEDT AVYYCAK | GPFRMRFRSFDY (SEQ ID NO. 4) | WGQGTLVTVSS |

VL sequence

| name of clone | Frame 1 | CDR1 | Frame 2 | CDR2 | Frame 3 | CDR3 | Frame 4 |
|---|---|---|---|---|---|---|---|
| H6 (SEQ ID NO. 5) | QSVLTQPPSASGTPG QRATISC | TGSSNIGSNSVS (SEQ ID NO. 6) | WYQQLPGTAPKL LIY | ANSNRPS (SEQ ID NO. 7) | GVPDRFSGSKSG TSASLAISGLRSE DEADYC | GTWDASLSAYV (SEQ ID NO. 8) | FGGGTKLTVL |

Fig. 2
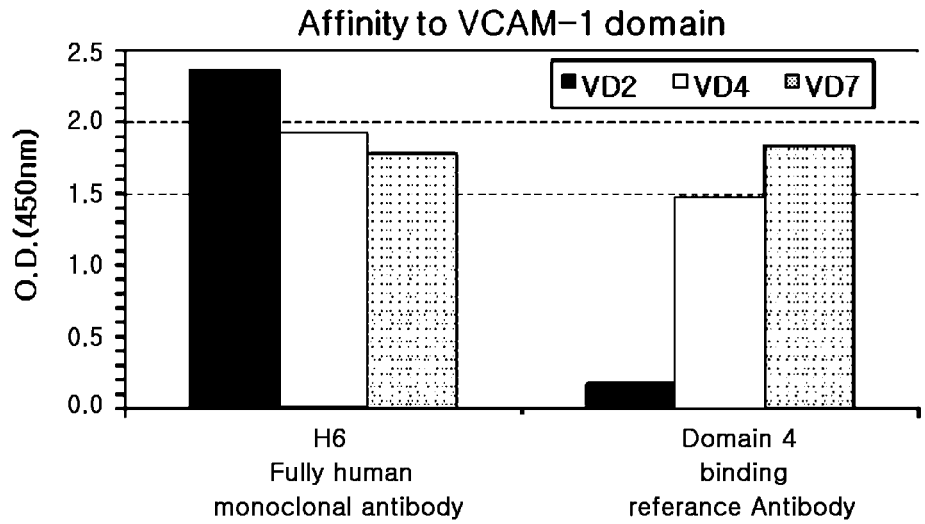
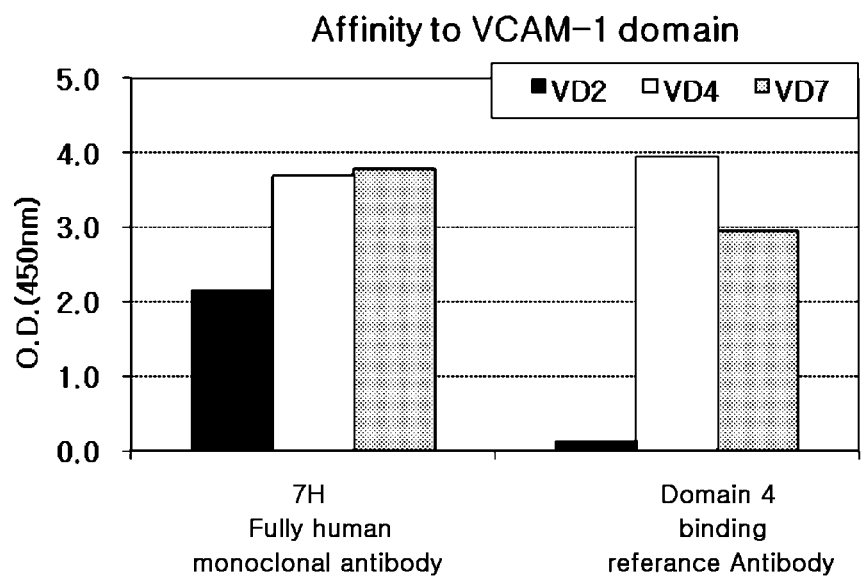
Fig. 3
| Antibody | 1:1 binding model | | | |
|---|---|---|---|---|
| | ka (1/Ms) | kd (1/s) | KD (nM) | $\chi^2$ |
| H6 | $5.05 \times 10^5$ | $3.19 \times 10^{-4}$ | 0.6 | 0.266 |
| 7H | $2.79 \times 10^5$ | $1.76 \times 10^{-3}$ | 6.3 | 0.56 |

Figure 9

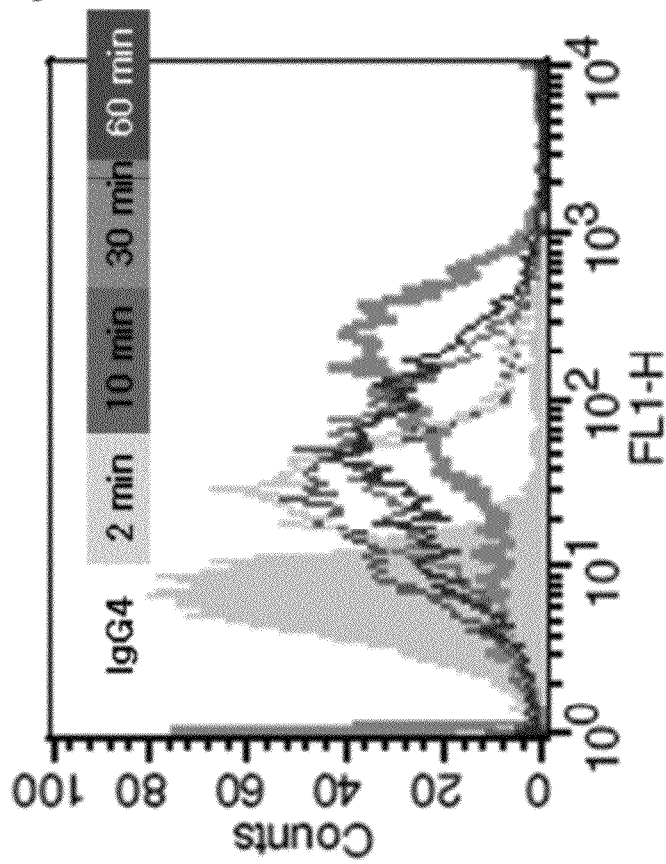

Figure 10

| SEQ ID NO | | |
|---|---|---|
| 21 | FR1: | EVQLVQSGGDLVKPGESLRLSCAAS |
| 10 | CDR-H1 | GFTFNDAWMT |
| 22 | FR2 | WVRQPPGKGLEWVG |
| 11 | CDR-H2 | RIKSTTDGGTTNYAAPVEG |
| 23 | FR3 | RFTISRDDSKNTLYLEMNSLRAEDTAVYYCAR |
| 12 | CDR-H3 | IPLFNHDSGGYHGAFDI |
| 24 | FR4 | WGQGTMVTVSS |
| 9 | Constant region | ASTKGPSVFPLAPCSRSTSESTAALGCLVKDYFPEPVTVSWNSGALTS GVHTFPAVLQSSGLYSLSSVVTVPSSSLGTKTYTCNVDHKPSNTKVD KRVESKYGPPCPPCPAPEFEGGPSVFLFPPKPKDTLMISRTPEVTCVV VDVSQEDPEVQFNWYVDGVEVHNAKTKPREEQFNSTYRVVSVLTV LHQDWLNGKEYKCKVSNKGLPSSIEKTISKAKGQPREPQVYTLPPSQ EEMTKNQVSLTCLVKGFYPSDIAVEWESNGQPENNYKTTPPVLDSD GSFFLYSRLTVDKSRWQEGNVFSCSVMHEALHNHYTQKSLSLSLGK |

| SEQ ID NO | | |
|---|---|---|
| 25 | FR1: | DIQMTQSPSSLAVSLGERATINC |
| 14 | CDR-L1 | KSSQSVLYSSNNKNYLA |
| 26 | FR2 | WYQQKPGQPPKLLIY |
| 15 | CDR-L2 | WASTRES |
| 27 | FR3 | GVPDRFSGSGSGTDFTLTISSLQPEDFASYYC |
| 16 | CDR-L3 | QESYSAPYT |
| 28 | FR4 | FGQGTKVEIKR |
| 13 | Constant region(Ck) | TVAAPSVFIFPPSDEQLKSGTASVVCLLNNFYPREAKVQWKVDN ALQSGNSQESVTEQDSKDSTYSLSSTLTLSKADYEKHKVYACEVTH QGLSSPVTKSFNRGEC |

**H&E staining
Liver**

Normal Chow
ip: PBS

High-Fat
ip: 4BT Ab
(10mg/kg)

High-Fat
ip: 7HT Ab
(1mg/kg)

High-Fat
ip: 7HT Ab
(10mg/kg)

**H&E staining
Kidney**

Normal Chow
ip: PBS

High-Fat
ip: 4BT Ab
(10mg/kg)

High-Fat
ip: 7HT Ab
(1mg/kg)

High-Fat
ip: 7HT Ab
(10mg/kg)

Fig. 23
H&E staining Spleen
Normal Chow
ip: PBS
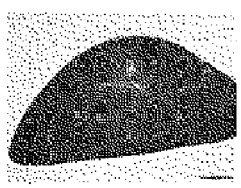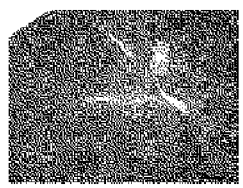
High-Fat
ip: 4BT Ab
(10mg/kg)
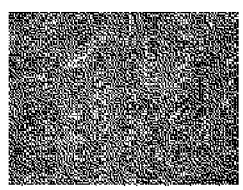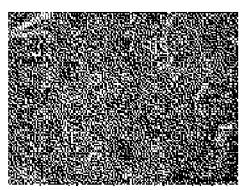
High-Fat
ip: 7HT Ab
(1mg/kg)
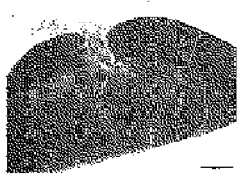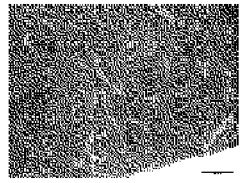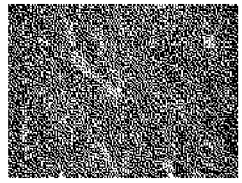
High-Fat
ip: 7HT Ab
(10mg/kg)
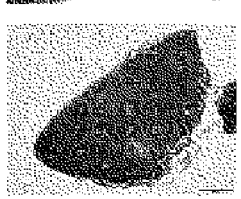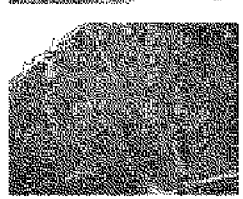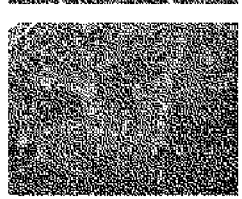

HUMAN RECOMBINANT MONOCLONAL ANTIBODY THAT SPECIFICALLY BINDS TO VCAM-1 AND INHIBITS ADHESION AND TRANSMIGRATION BETWEEN LEUKOCYTES AND ENDOTHELIAL CELLS

RELATED APPLICATIONS

The present application claims the benefit of priority of International Application No. PCT/KR2010/007303 filed Oct. 22, 2010, which claims priority to Korean Patent Application No. 10-2009-0101254, filed Oct. 23, 2009 and Korean Patent Application No. 10-2010-0103523, filed Oct. 22, 2010. The entire contents of each of the above documents are incorporated herein by reference.

TECHNICAL FIELD

The present invention relates to a human recombinant monoclonal antibody that specifically binds to human Vascular Cell Adhesion Molecule-1 (VCAM-1) to inhibit adhesion between leukocytes and activated endothelial cells and transmigration of leukocytes through the activated endothelial cells, and a prophylactic and therapeutic composition for inflammatory disease or cancer comprising the same.

BACKGROUND ART

During migration from the blood stream to the tissue, immune cells including leukocytes pass through activated endothelial cells to induce immune responses, and many cell adhesion molecules (CAMs), such as integrins, selectins, ICAMs (intracellular adhesion molecule) and VCAMs (vascular cell adhesion molecule), are involved in the adhesion of leukocytes to endothelial cells and their migration to the tissue. Cell adhesion molecules are functionally divided into selectins involved in interaction between leukocytes and endothelial cells, integrins involved in adhesion of leukocytes to endothelial cells, and immunoglobulins such as ICAM and VCAM. These cell adhesion molecules play important roles in many physiological responses such as immune responses, inflammation, and thrombosis.

VCAM-1 is one of the vascular endothelial cell adhesion molecules, which interacts with integrin (VLA-4) expressed on the surfaces of most leukocytes, excluding neutrophils. VCAM-1 is expressed by inflammatory signals, and induces attachment of leukocytes to the vascular endothelial cells and the subsequent transendothelial migration of leukocytes into the damaged tissue.

Despite recent attention to VCAM-1-VLA-4 interaction, the development of a neutralizing antibody to VCAM-1 has not been actively studied. Although M/K-2.7, a monoclonal antibody to mouse VCAM-1, has recently been developed and shows an inhibitory effect on arthritis in collagen-induced arthritis mouse model, the antibody is specific only to mouse model, and thus the usefulness of the antibody should be further tested for clinical application.

Further, VCAM-1 consists of seven IgG-like domains and its domains 1 and 4 are substantially involved in binding with its ligand, integrin ($\alpha 4\beta 1$ or $\alpha 4\beta 7$) (1995, PNAS, 92:p5714; 1995, The journal of immunology, 155: p3135 et al.).

In this regard, there is an urgent need to develop a fully human monoclonal antibody which inhibits the interaction between VCAM-1 antigen and integrin to effectively inhibit adhesion and transmigration of leukocytes to endothelial cells, and minimizes the risk of immunogenicity.

DISCLOSURE OF INVENTION

Technical Problem

Accordingly, the present inventors have developed a human VCAM-1-specific human recombinant monoclonal antibody having human-derived heavy chain (VH) and light chain (VL) domains, in which the human recombinant monoclonal antibody specifically recognizes VCAM-1 expressed on the surface of human endothelial cell and binds to the domain 1 or 2 of VCAM-1 antigen to show a strong activity of inhibiting the interaction between U397 promonocytic leukocytes and activated endothelial cells, thereby completing the present invention.

Solution to Problem

It is an object of the present invention to provide a human recombinant monoclonal antibody that specifically binds to human Vascular Cell Adhesion Molecule-1 (VCAM-1) to inhibit adhesion between leukocytes and activated endothelial cells and transmigration of leukocytes through the activated endothelial cells.

It is another object of the present invention to provide a method of providing information for the diagnosis of inflammatory disease, cardiovascular disease or cancer, comprising the step of detecting antigen-antibody reaction between the human recombinant monoclonal antibody and VCAM-1 in a biological sample of a subject suspected of having inflammatory disease or cancer.

It is still another object of the present invention to provide a method of inhibiting adhesion between leukocytes and activated endothelial cells and transmigration of leukocytes through the activated endothelial cells using the human recombinant monoclonal antibody.

It is still another object of the present invention to provide a diagnostic composition for inflammatory disease, cardiovascular disease or cancer, comprising the human recombinant monoclonal antibody.

It is still another object of the present invention to provide a prophylactic or therapeutic composition for inflammatory disease, cardiovascular disease or cancer, comprising the human recombinant monoclonal antibody and a pharmaceutically acceptable carrier.

It is still another object of the present invention to provide a method for treating inflammatory disease, cardiovascular disease or cancer, comprising the step of administering the prophylactic or therapeutic composition for inflammatory disease or cancer.

Advantageous Effects of Invention

The human recombinant monoclonal antibody according to the present invention shows a strong affinity to VCAM-1 expressed on human endothelial cell, and effectively inhibits VCAM-1-mediated adhesion between leukocytes and activated endothelial cells and transmigration of leukocytes through the activated endothelial cells, thereby being used for the prevention and treatment of inflammatory disease such as asthma and arthritis, transplant rejection, cardiovascular disease, and cancer.

BRIEF DESCRIPTION OF DRAWINGS

FIG. 1 shows the amino acid sequences of variable regions of human recombinant monoclonal antibody according to one embodiment of the present invention. The VH sequence of clone H6 (SEQ ID NO. 1) is shown as framework regions and individual CDRs. For the VH sequence, CDR1 (SEQ ID NO. 2), CDR2 (SEQ ID NO. 3) and CDR3 (SEQ ID NO. 4) are shown. The VL seeuence of clone H6 (SEQ ID NO. 5) is also shown as framework regions and individual CDRs. For the VL sequence, CDR1 (SEQ ID NO. 6), CDR2 (SEQ ID NO. 7) and CDR3 (SEQ ID NO. 8) are shown.

FIG. 2 is the result of ELISA (Enzyme-linked immunosorbent assay) showing the affinity of antigen-specific anti VCAM-1 human monoclonal antibodies to antigen according to their human VCAM-1 domains, in which VD2 represents a recombinant human VCAM-1 domain D1-D2/Fc chimera, VD4 represents a recombinant human VCAM-1 domain D11-D44/Fc chimera, and VD7 represents recombinant human VCAM-1 domain D1-D7/Fc chimera;

FIG. 3 shows the binding capability or affinity of human VCAM-1 antigen-specific anti VCAM-1 human monoclonal antibodies to antigens, in which the antigen-antibody affinity was determined by 1:1 binding mode using a BIACORE instrument (BIACORE AB, Sweden) to calculate an antigen-antibody affinity constant, KD value;

FIG. 9 is the result of analyzing internalization according to one embodiment of the present invention;

FIG. 10 shows heavy chain and CDR sequences of the human recombinant monoclonal antibody according to one embodiment of the present invention;

FIG. 23 is the result of pathological analysis of spleen section by H&E staining in order to test toxicity of VCAM-1 antibody injection according to one embodiment of the present invention.

BEST MODE FOR CARRYING OUT THE INVENTION

Figure 4:
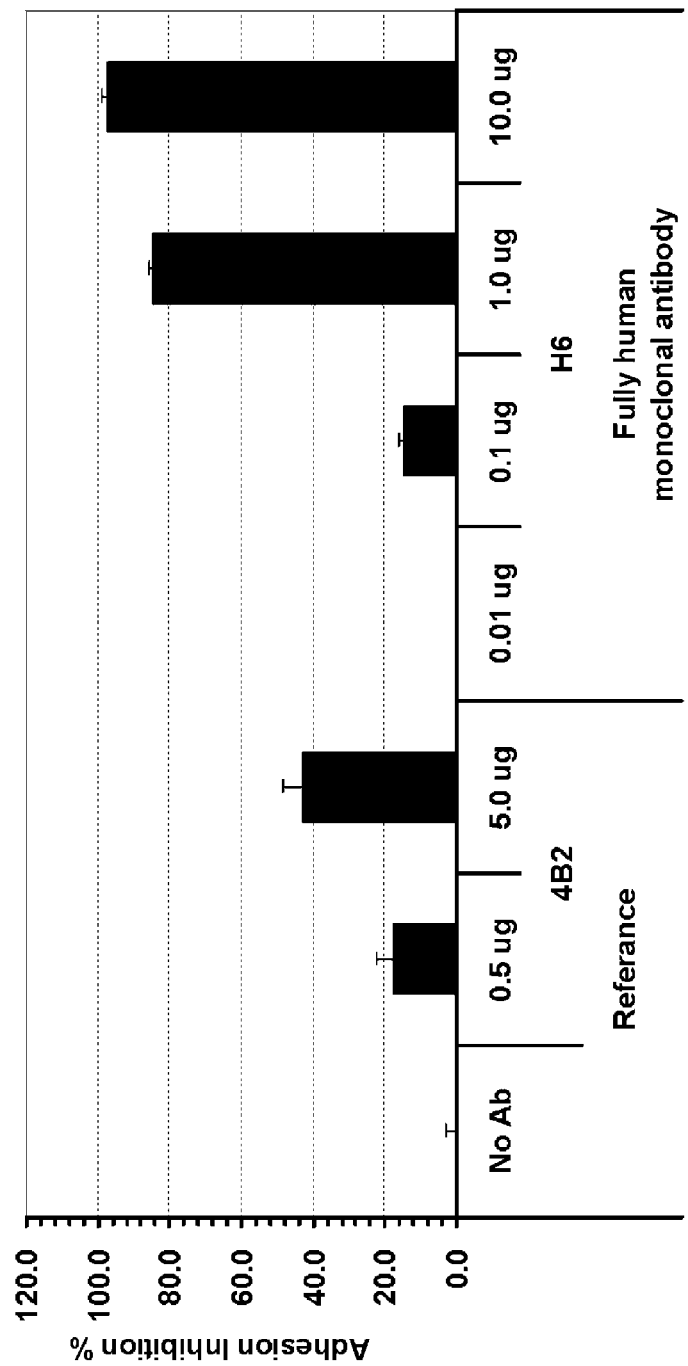
FIG. 4 is the result of analyzing the inhibitory activity of anti VCAM-1 human monoclonal antibodies on the adhesion between purified human recombinant VCAM-1 antigens and human leukocytes, in which their inhibitory activity is determined by reduction in fluorescence intensity, compared to that of non-antibody-treated group.

Hereinafter, the present invention will be described in detail with reference to Examples. However, the following Examples are provided only for the purpose of illustrating the present invention, and accordingly it is not intended that the present invention is limited thereto.

In one aspect to achieve the above objects, the present invention relates to a human recombinant monoclonal antibody, characterized in that it specifically binds to human Vascular Cell Adhesion Molecule-1 (VCAM-1) to inhibit adhesion between leukocytes and activated endothelial cells and transmigration of leukocytes through the activated endothelial cells.

Description of the following terms is provided for a better understanding of the specification, and the terms as used herein are provided for illustrative purposes only, and the invention is not intended to be limited by these terms. It should be noted that, as used in this specification and the appended claims, singular articles are intended to include a plurality of objects unless the context clearly indicates otherwise.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., dispecific antibodies).

The term "antibody" also includes antigen binding forms of antibodies, including fragments with antigen-binding capability (e.g., Fab', F(ab')2, Fab, Fv and rIgG). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992, J. Immunol. 148:15467), Pack and Pluckthun (1992, Biochemistry 31:1579), Hollinger et al. (1993, supra), Gruber et al. (1994, J. Immunol.: 5368), Zhu et al. (1997, Protein Sci. 6:781), Hu et al. (1996, Cancer Res. 56:3055), Adams et al. (1993, Cancer Res. 53:4026 and McCartney et al. (1995, Protein Eng. 8:301).

Also, the term "monoclonal antibody" as used herein, refers to an antibody molecule that has been obtained from a substantially identical antibody clone, which shows single-binding specificity and affinity for a specific epitope.

Typically, an immunoglobulin has a heavy and light chain. Each heavy and light chain contains a constant region and a variable region (the regions are also known as "domains"). Light chain and heavy chain variable regions contain three hypervariable regions called "complementarity-determining regions" (hereinbelow, referred to as "CDRs") and four "framework" regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located.

As used herein, the term "humanized antibody" is a molecule derived from human immunoglobulin, and means that all amino acid sequences constituting an antibody, including complementarity-determining regions and framework regions, are composed of human immunoglobulin. The term "human recombinant monoclonal antibody" refers to an antibody molecule of single molecular composition, derived from human immunoglobulin.

Humanized antibodies generally have at least three potential advantages for use in human therapy. First, it may interact better with the human immune system, e.g., to destroy target cells more efficiently by complement-dependent cytotoxicity (CDC) or antibody-dependent cellular cytotoxicity (ADCC). Second, the human immune system does not recognize the antibody as foreign. Third, the half-life in the human circulation will be similar to that of naturally occurring human antibodies, allowing smaller and less frequent doses to be given. Therefore, the human monoclonal antibodies according to the present invention show a strong affinity to VCAM-1 expressed on human endothelial cells, and effectively inhibit leukocyte adhesion to activated endothelial cells expressing VCAM-1. In addition, since their heavy chain and light chain domains are all derived from human cells to show low immunogenicity, the human monoclonal antibodies according to the present invention can be used for the treatment of inflammatory disease or cancer, and the inflammatory disease may be selected from tumor necrosis factor-α(TNF-α-mediated disease, intestinal disease, arteriosclerosis, and myocardial infarction, and preferably selected from the group consisting of asthma, diabetes, uveitis, ankylosing spondylitis, sepsis, endotoxin shock, hemodynamic shock, sepsis syndrome, ischemic reperfusion injury, malaria infection, mycobacterial infection, meningitis, psoriasis, congestive heart failure, fibrotic diseases, Kachexie, transplant rejection, cancer, autoimmune diseases, AIDS-related opportunistic infection, arthritis, rheumatoid spondylitis, gout, ankylosing gout, Crohn's disease, ulcerative trigonitis, multiple sclerosis, erythema nodosum leprosum (ENL), radiation injury and hyperoxia-induced alveolar damage.

According to the preferred embodiment of the present invention, the human recombinant monoclonal antibody of the present invention may include a heavy chain variable region that contains CDR1 having the amino acid sequence of SEQ ID NO. 2; CDR2 having the amino acid sequence of SEQ ID NO. 3; and CDR3 having the amino acid sequence of SEQ ID NO. 4. Meanwhile, the human recombinant monoclonal antibody of the present invention may be prepared by attaching framework region (FR) of the known therapeutic antibody to the complementarity-determining region (CDR). More preferably, the human recombinant monoclonal antibody of the present invention may be a human recombinant monoclonal antibody that contains the heavy chain amino acid sequence as defined by SEQ ID NO. 1 (see FIG. 1).

Further, according to the preferred embodiment of the present invention, the human recombinant monoclonal antibody of the present invention may include a light chain variable region that contains CDR1 having the amino acid sequence of SEQ ID NO. 6; CDR2 having the amino acid sequence of SEQ ID NO. 7; and the amino acid sequence of SEQ ID NO. 8. Meanwhile, the human recombinant monoclonal antibody of the present invention may be prepared by attaching the framework region (FR) of the known therapeutic antibody to the complementarity-determining region (CDR). More preferably, the human recombinant monoclonal antibody of the present invention may be a human recombinant monoclonal antibody that contains the light chain amino acid sequence as defined by SEQ ID NO. 5 (see FIG. 1).

More preferably, the human recombinant monoclonal antibody of the present invention may be a human monoclonal antibody that contains all of the light chain and heavy chain variable regions. That is, the human recombinant monoclonal antibody of the present invention may include a heavy chain variable region that contains heavy chain CDR1 as defined by SEQ ID NO. 2; heavy chain CDR2 as defined by SEQ ID NO. 3; and heavy chain CDR3 as defined by SEQ ID NO. 4, and a light chain variable region that contains light chain CDR1 as defined by SEQ ID NO. 6; light chain CDR2 as defined by SEQ ID NO. 7; and light chain CDR3 as defined by SEQ ID NO. 8. Meanwhile, the human recombinant monoclonal antibody of the present invention may be prepared by attaching the framework region (FR) of the known therapeutic antibody to the complementarity-determining region (CDR). Most preferably, the human recombinant monoclonal antibody of the present invention may be a human recombinant monoclonal antibody that contains the heavy chain amino acid sequence as defined by SEQ ID NO. 1 and the light chain amino acid sequence as defined by SEQ ID NO. 5 (see FIG. 1).

Additionally, according to the preferred embodiment of the present invention, the human recombinant monoclonal antibody of the present invention may include a heavy chain variable region that contains CDR1 having the amino acid sequence of SEQ ID NO. 10; CDR2 having the amino acid sequence of SEQ ID NO. 11; and CDR3 having the amino acid sequence of SEQ ID NO. 12. Meanwhile, the human recombinant monoclonal antibody of the present invention may be prepared by attaching the framework region (FR) of the known therapeutic antibody to the complementarity-determining region (CDR). More preferably, the human recombinant monoclonal antibody of the present invention may be a human recombinant monoclonal antibody that contains the heavy chain amino acid sequence as defined by SEQ ID NO. 9 (see FIG. 10).

Further, according to the preferred embodiment of the present invention, the human recombinant monoclonal antibody of the present invention may include a light chain variable region that contains CDR1 having the amino acid sequence of SEQ ID NO. 14; CDR2 having the amino acid sequence of SEQ ID NO. 15; and the amino acid sequence of SEQ ID NO. 16. Meanwhile, the human recombinant monoclonal antibody of the present invention may be prepared by attaching the framework region (FR) of the known therapeutic antibody to the complementarity-determining region (CDR). More preferably, the human recombinant monoclonal antibody of the present invention may be a human recombinant monoclonal antibody that contains the light chain amino acid sequence as defined by SEQ ID NO. 13 (see FIG. 11).

More preferably, the human recombinant monoclonal antibody of the present invention may be a human monoclonal antibody that contains all of the light chain and heavy chain variable regions. That is, the human recombinant monoclonal antibody of the present invention may include a heavy chain variable region that contains heavy chain CDR1 as defined by SEQ ID NO. 10; heavy chain CDR2 as defined by SEQ ID NO. 11; and heavy chain CDR3 as defined by SEQ ID NO. 12, and a light chain variable region that contains light chain CDR1 as defined by SEQ ID NO. 14; light chain CDR2 as defined by SEQ ID NO. 15; and light chain CDR3 as defined by SEQ ID NO. 16. Meanwhile, the human recombinant monoclonal antibody of the present invention may be prepared by attaching the framework region (FR) of the known therapeutic antibody to the complementarity-determining region (CDR). Most preferably, the human recombinant monoclonal antibody of the present invention may be a human recombinant monoclonal antibody that contains the heavy chain amino acid sequence as defined by SEQ ID NO. 9 and the light chain amino acid sequence as defined by SEQ ID NO. 13 (see FIG. 11).

In this connection, the human recombinant monoclonal antibody provides an affinity to human VCAM-1, in accordance with one preferred embodiment, an association/dissociation constant (KD value) of human recombinant monoclonal antibody to human VCAM-1 antigen may be $0.1 \times 10^{-9}$ M to $7.0 \times 10^{-9}$ M, which can be obtained by determining the association/dissociation constant (KD value) of each antibody to human VCAM-1 antigen using a BIACORE analysis. That is, human VCAM-1 antigen as a ligand was immobilized to a sensor chip (Sensor chip CM5, BIACORE, BR-1003-99), and then each dilution of the antibodies was applied to the immobilized ligand using a BIACORE instrument to induce association and dissociation between antigen and antibody, thereby determining the association(Ka)/dissociation (Kd) constant KD value, and chi square $\Delta(\chi 2)$ value that is a statistical value associated with reliance.

The human recombinant monoclonal antibody of the present invention can easily be produced by well-known methods for producing a monoclonal antibody. For example, the method for preparing a monoclonal antibody may be performed by producing a hybridoma using B leukocytes obtained from immunized animals (Koeher and Milstein, 1976, Nature, 256:495), or using a phage display method, but is not limited thereto.

An antibody library using a phage display is a method of expressing an antibody on the surface of a phage with genes of the antibody directly obtained from B lymphocytes without preparation of hybridoma. Many of the difficulties associated with generating monoclonal antibodies by B-cell immortalization can be overcome by a phage display method.

A conventional phage display comprises: 1) inserting an oligonucleotide having a random sequence into the region corresponding to the N-terminus of a phage coat protein pIII (or pIV); 2) expressing a fusion protein of a natural coat protein and a polypeptide coded by said oligonucleotide having a random sequence; 3) treating a receptor material that can bind to the polypeptide coded by said oligonucleotide; 4) eluting peptide-phage particles bound to the receptors using low pH or a molecule which has binding competitiveness; 5) amplifying the eluted phage in a host cell by panning; 6) repeating said steps to obtain desired amounts of phage; and 7) determining the sequence of an active peptide with the DNA sequencing of phage clones selected by panning.

In a preferred embodiment, a preparation method of the human recombinant monoclonal antibody of the present invention may be performed by a phage display method. A person skilled in the art to which the present invention pertains can perform the above steps easily referring to well-known phage display techniques, which are disclosed in, for example, Barbas et al. (METHODS: A Companion to Methods in Enzymology 2: 119, 1991 and J. Virol. 2001 July; 75(14):6692-9) and Winter et al. (Ann. Rev. Immunol. 12:433, 1994). A phage which can be used for constructing the antibody library may be a filamentous phage, for example, fd, M13, f1, If1, Ike, Zj/Z, Ff, Xf, Pf1 and Pf3, but is not limited thereto. Also, a vector, which can be used for the expression of a heterogeneous gene on the surface of the filamentous phage, may be a phage vector such as fUSE5, fAFF1, fd-CAT1, or fdtetDOG, or a phagemid vector such as pHEN1, pComb3, pComb8 or pSEX, but is not limited thereto.

Further, a helper phage, which can be used for providing a natural coat protein required for successful re-infection of recombinant phage, may be exemplified by M13K07 or VSCM13, but is not limited thereto.

In the specific Example of the present invention, the human antibody specific to human VCAM-1 was obtained as scFv by phage display technology, and screened as a mono phage clone, thereby obtaining 20 types of monoclone phages being specific to human VCAM-1.

In the specific Example of the present invention, a molecular weight and purity of VCAM-1 obtained by recombinant technique were examined, and then used for preparation of a monoclonal antibody. VCAM-1 was reacted with library phage from human naive scFv library cells having diversity, followed by panning and screening of monoclonal antibodies strongly binding to VCAM-1 antigen (see Table 1). The selected monoclonal antibodies were confirmed by fingerprinting, followed by sequencing to confirm CDR regions of VH and VL of the antibody. Homology between the above antibody and germ line antibody group was investigated using the Ig BLAST program of NCBI website (www.ncbi.nlm.nih.gov/igblast). As a result, 20 types of phage antibodies being specific to VCAM-1 were obtained.

Further, in accordance with the specific Example of the present invention, an expression vector containing a polynucleotide encoding the heavy chain and light chain of the selected 20 types of human antibody phage or the fragment thereof having immunological activity was constructed. Upon construction of the expression vector, expression regulatory elements, such as a promoter, a terminator, and an enhancer, and a sequence for targeting membranes or secretion can be properly selected and used in combination for purpose, depending on a host cell intended to produce the light chain and heavy chain of the human antibody or the fragment thereof.

The expression vector of the present invention includes a plasmid vector, a cosmid vector, a bacteriophage vector, a viral vector or the like, but is not limited thereto. A suitable expression vector includes a signal sequence or a leader sequence for targeting membranes or secretion as well as expression regulatory elements, such as a promoter, an operator, an initiation codon, a stop codon, a polyadenylation signal and an enhancer, and can be constructed in various forms depending on the purpose thereof.

Further, according to one embodiment of the present invention, the present invention provides a method of identifying the location of the domains of human VCAM-1 antigen, which bind with the human recombinant monoclonal antibody. It has been reported that VCAM-1 consists of seven IgG-like domains and its domains 1 and 4 are substantially involved in binding with its ligand, integrin ($\alpha 4\beta 1$ or $\alpha 4\beta 7$). Therefore, to confirm the epitope of VCAM-1 antigen specific to the human recombinant monoclonal antibody according to the present invention, the following procedures were performed in the specific Example.

The present inventors analyzed antigen-binding regions of 20 types of antibodies by ELISA, after expressing and purifying each domain (VD2, VD4, VD7) of human VCAM-1 antigen. As a result, the antigen-binding regions vary depending on the type of antibodies, and among them, the antibodies H6 and 7HT binding to domain 1 or 2 was obtained (see FIG. 2).

Further, the human recombinant monoclonal antibody according to the present invention provides an affinity to human VCAM-1 antigen. In the specific Example of the present invention, an association/dissociation constant (KD value) of the antibody to human VCAM-1 antigen was determined by a BIACORE analysis to confirm the affinity. It was found that antibodies H6 and 7HT have a strong affinity to human VCAM-1 (see FIG. 3). As a result, it was found that the H6 antibody has an excellent binding capacity to human VCAM-1 antigen to a level of approximately 0.6 nM, and the 7HT antibody has a binding capacity to human VCAM-1 antigen to a level of approximately 6.3 nM.

Therefore, the human recombinant monoclonal antibody according to the present invention can be used in the composition and method for detecting VCAM-1, comprising the step of detecting antigen-antibody reaction between the human recombinant monoclonal antibody and VCAM-1 in a biological sample.

Figure 5:
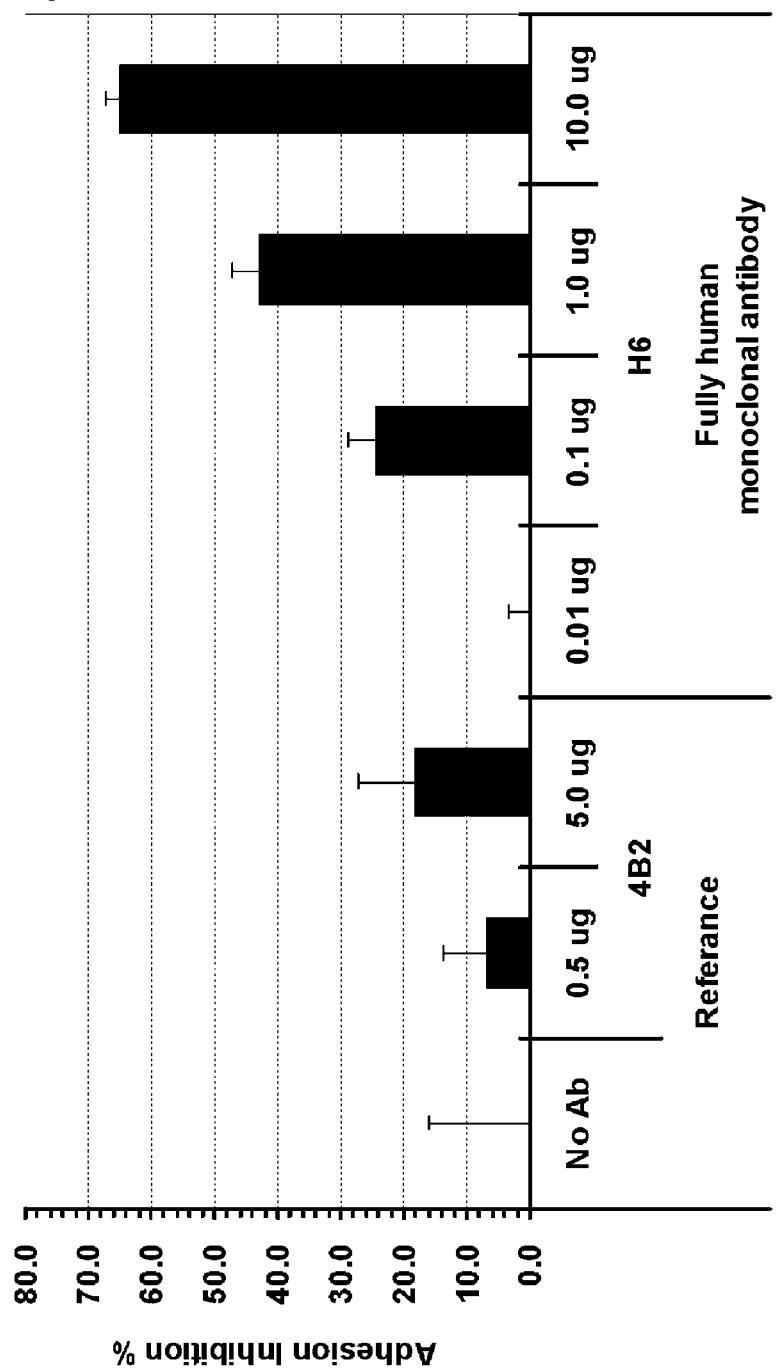
FIG. 5 is the result of analyzing the inhibitory activity of anti VCAM-1 human monoclonal antibodies on the adhesion between human leukocytes and human endothelial cells activated with TNF-α (Tumor necrosis factor-α, in which their inhibitory activity is determined by reduction in fluorescence intensity, compared to that of non-antibody-treated group.

Further, in the specific Example of the present invention, the human recombinant monoclonal antibody (H6) according to the present invention was found to inhibit the adhesion between human leukocytes (U937 cell) and human endothelial cells (HUVEC) stimulated with recombinant human VCAM-1 or human TNF-$\alpha$, since the interaction between leukocytes and activated endothelial cells is mediated by VCAM-1. In accordance with one embodiment of the present invention, a human VCAM-1-immobilized solid support plate or a HUVEC monolayer plate is treated with the antibodies at various concentrations. To examine whether the antibodies inhibit binding of the fluorescence-labeled U937 cell and the antigen, fluorescence intensity was measured. As a result, the antibody showed an inhibitory activity on the adhesion. In particular, the antibody was found to exhibit strong inhibitory activity even at a low concentration (see FIGS. 4 and 5).

Figure 6:
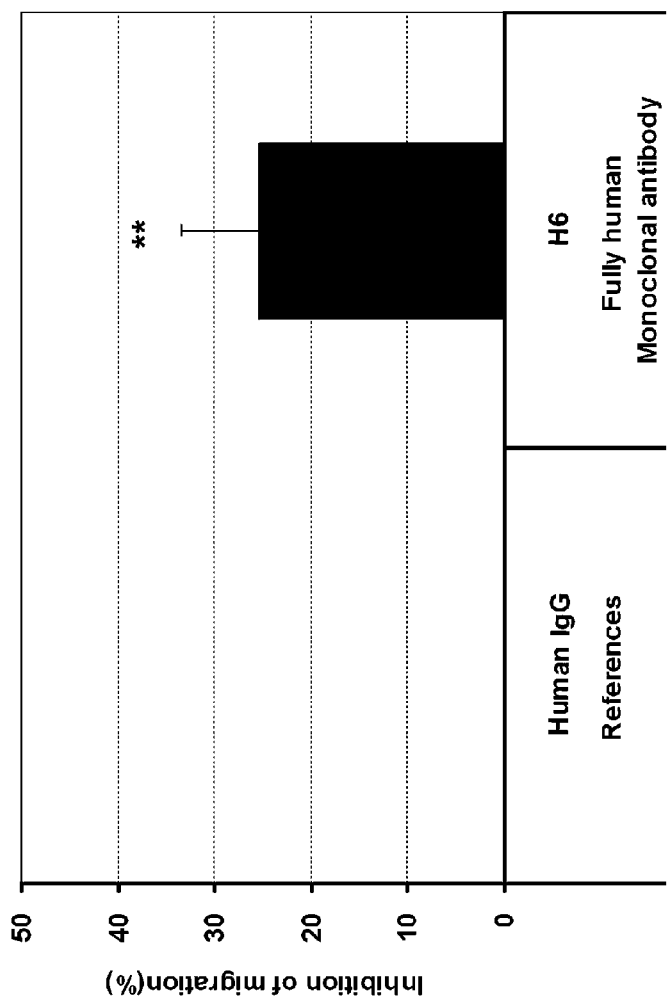
FIG. 6 is the result of analyzing the inhibitory activity of anti VCAM-1 human monoclonal antibodies on the transmigration of human leukocytes through human endothelial cells activated with TNF-α (Tumor necrosis factor-α), in which their inhibitory activity is determined by reduction in the number of transmigrated leukocytes, compared to that of non-antibody-treated group.
Figure 7:
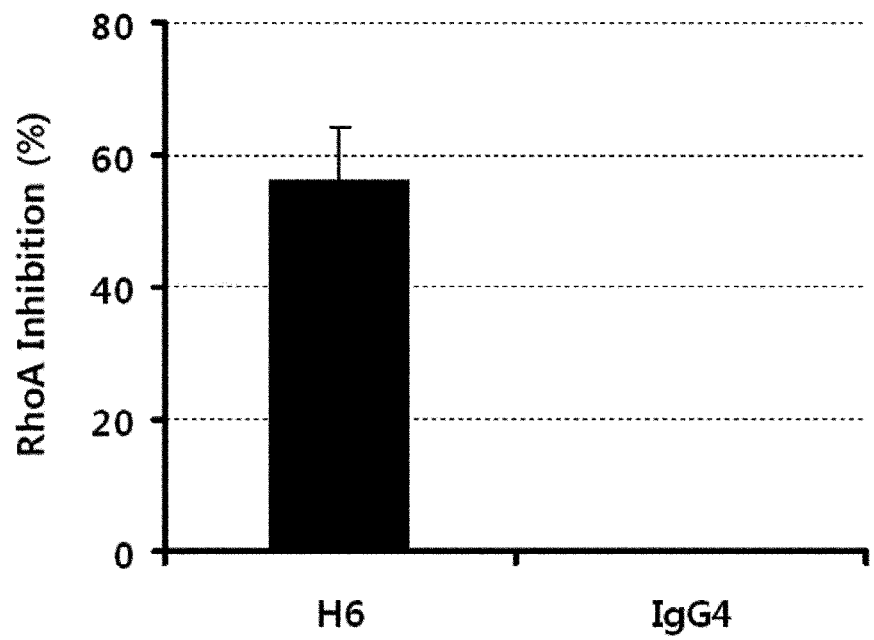
FIG. 7 is the result of analyzing the inhibitory activity on RhoA (Ras homolog gene family, member A) activity according to one embodiment of the present invention.
Figure 8:
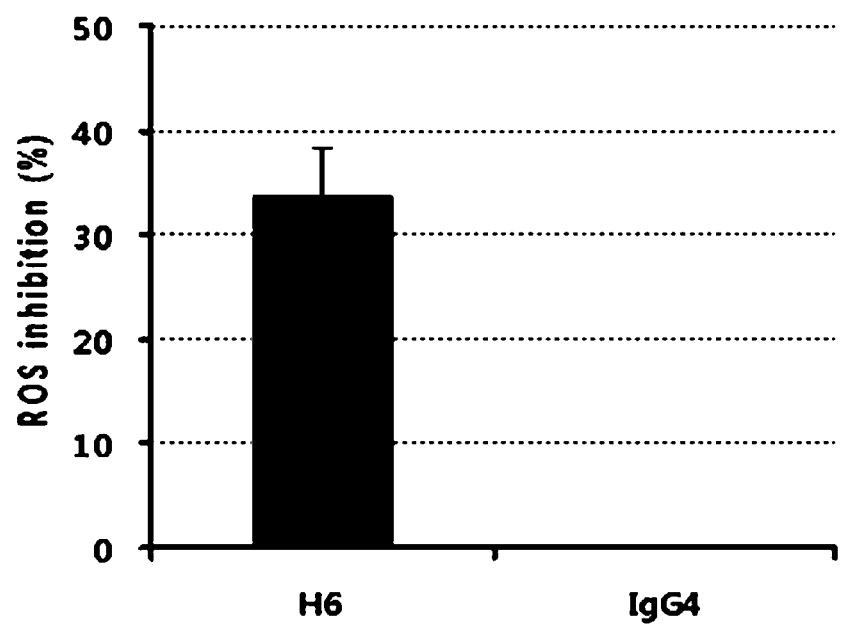
FIG. 8 is the result of analyzing the inhibitory activity on ROS (Reactive oxygen species) activity according to one embodiment of the present invention.

Moreover, in the present invention, it was confirmed that the human recombinant monoclonal antibody according to the present invention inhibits the permeability of human leukocytes into human endothelial cell monolayer among the interactions between human leukocytes (U937 cell) and human endothelial cells (HUVEC) stimulated with human TNF-$\alpha$, since the interaction between leukocytes and activated endothelial cells is mediated by VCAM-1. In the example of the present invention, HUVEC monolayer plated on a transwell plate was treated with the antibodies, and then the permeability of HUVEC monolayer by U937 cells was confirmed by counting the number of U937 cells collected in the bottom of the transwell. As a result, the above antibody showed a strong inhibitory activity on the permeability (see FIG. 6).

Figures 11, 12:
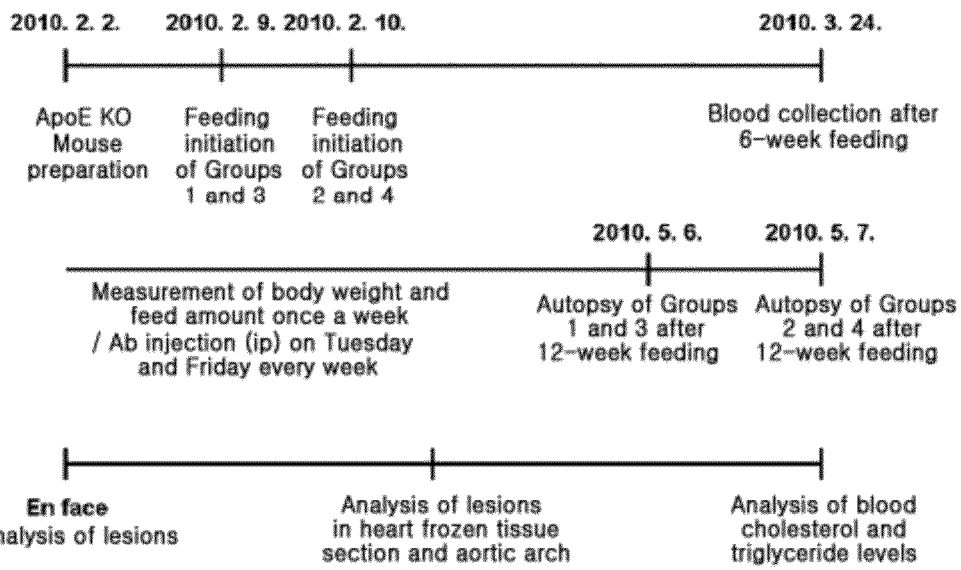
FIG. 11 shows light chain and CDR sequences of the human recombinant monoclonal antibody according to one embodiment of the present invention.
FIG. 12 shows a summary of animal experimentation according to one embodiment of the present invention.
Figure 14:
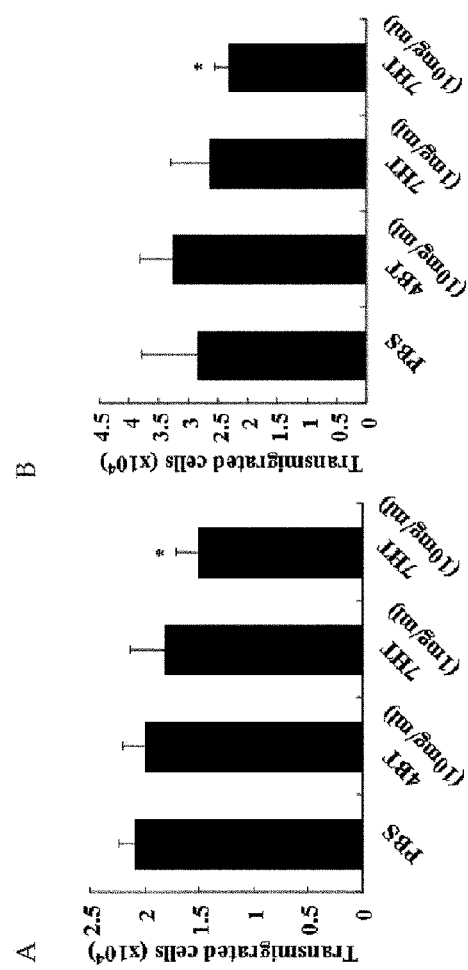
FIG. 14 is the result of analyzing inhibitory effect of VCAM-1 Ab on inflammatory cell transmigration by in vitro transmigration assay according to one embodiment of the present invention, in which (A) shows a graph of the number of transmigrated cells after 4 hrs, and (B) shows a graph of the number of transmigrated cells after 18 hrs.
Figure 15:
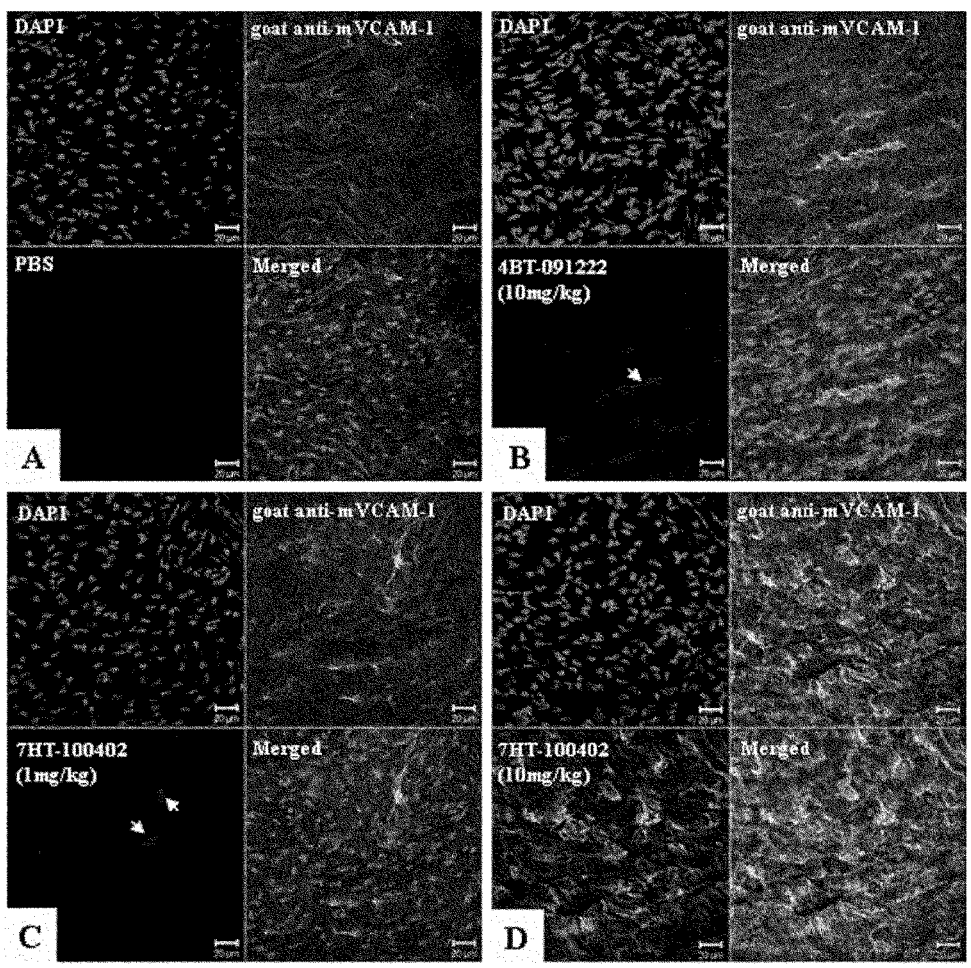
FIG. 15 is the result of en face confocal microscopy to test the in vivo binding capacity of VCAM-1 Ab (7HT) according to one embodiment of the present invention ((A) PBS, (B) high dose control Ab, (C) low dose VCAM-1 Ab, (D) high dose VCAM-1 Ab)
Figure 17:
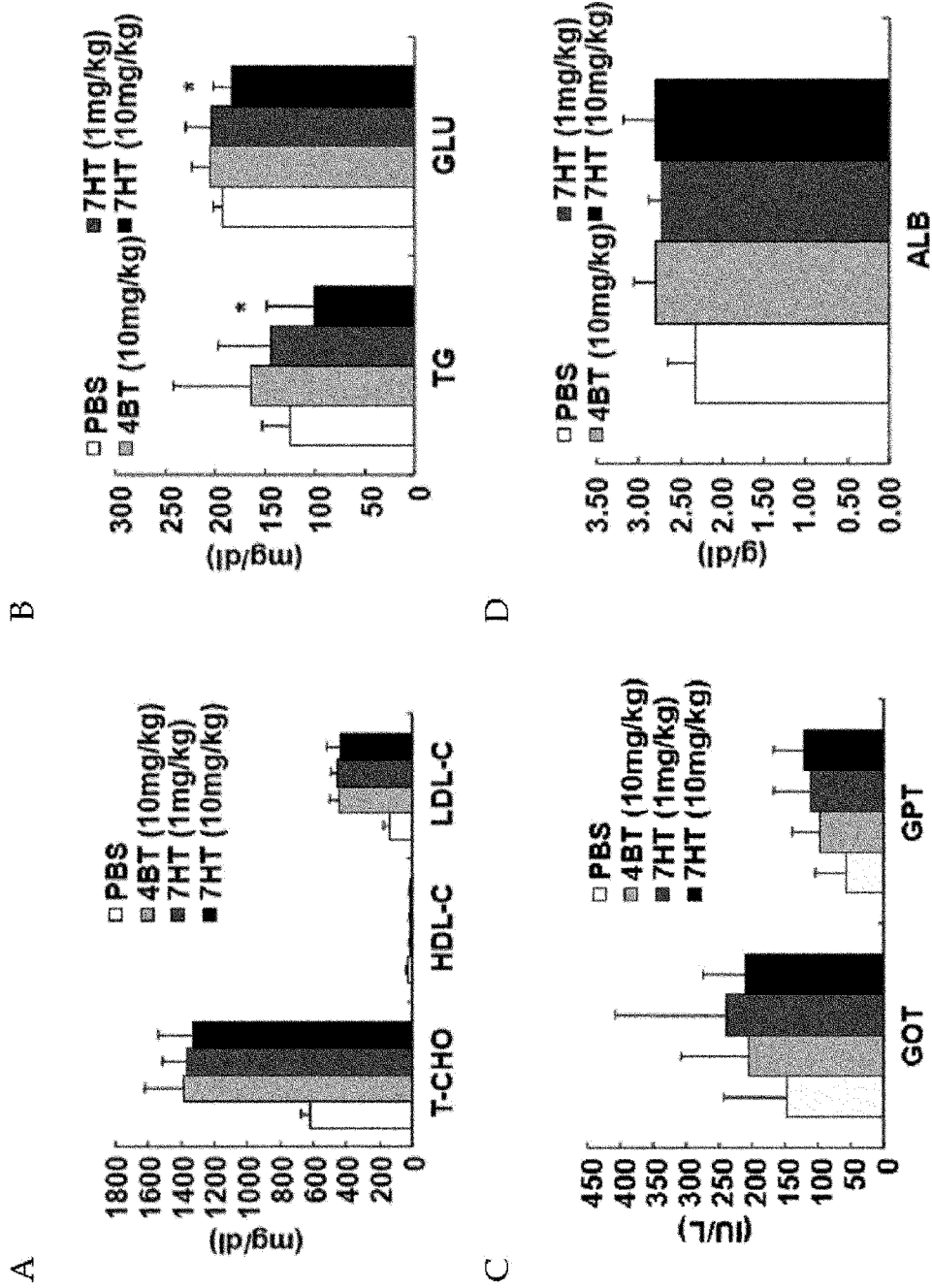
FIG. 17 is the result of hematologic analysis of mouse blood according to one embodiment of the present invention ((A) total cholesterol level (T-CHO), HDL-cholesterol level (HDL-C) and LDL-cholesterol level (LDL-C). (B) Triglyceride level (TG) and glucose level (GLU). (C) glutamic oxaloacetic transaminase level (GOT) and glutamic pyruvic transminase level (GPT). (D) albumin level (ALB))
Figure 18:
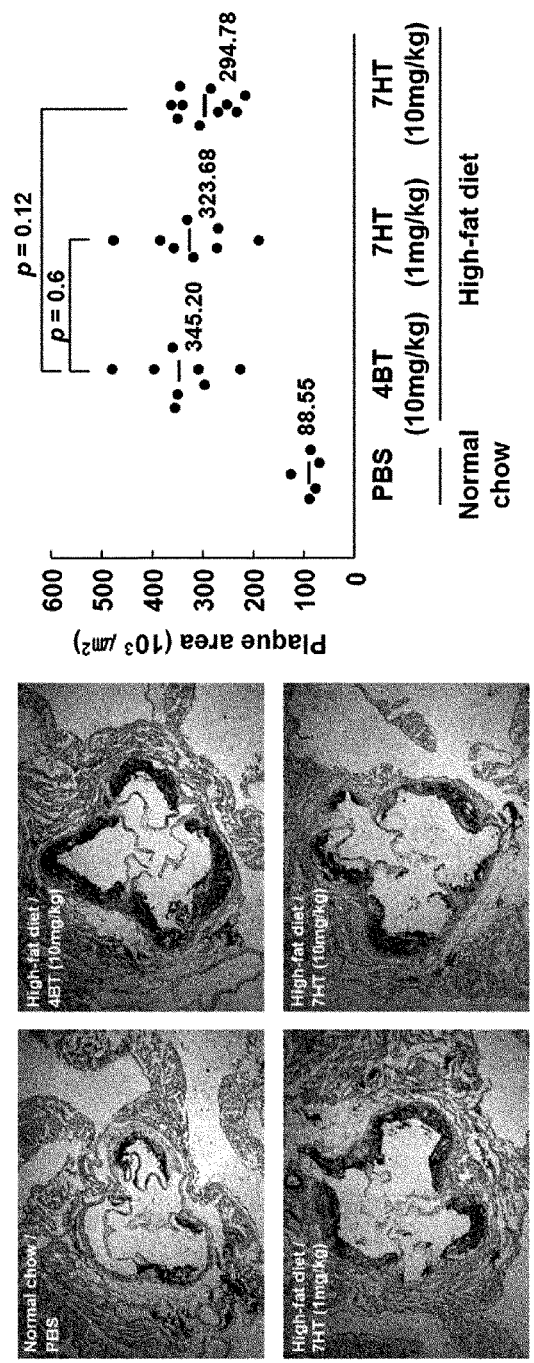
FIG. 18 is the result of measuring formation of atherosclerotic plaque in the aortic arch and size thereof according to one embodiment of the present invention.
Figure 19:
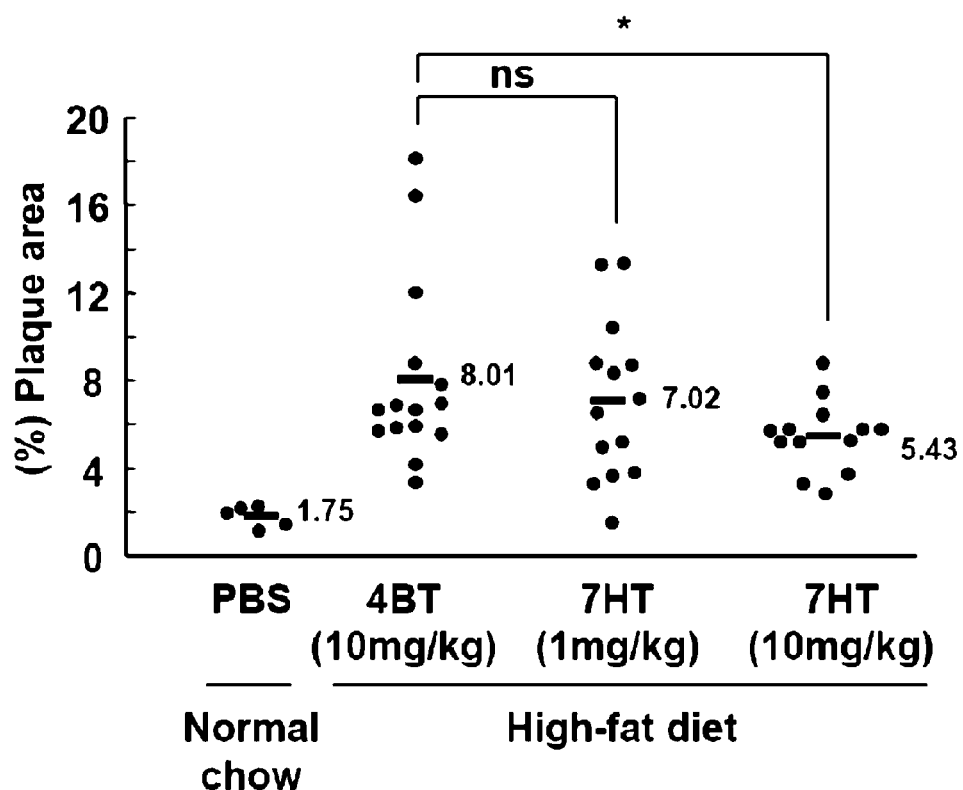
FIG. 19 is a graph showing the result of En face method to analyze atherosclerotic plaque formed in the artery according to one embodiment of the present invention.
Figure 20:
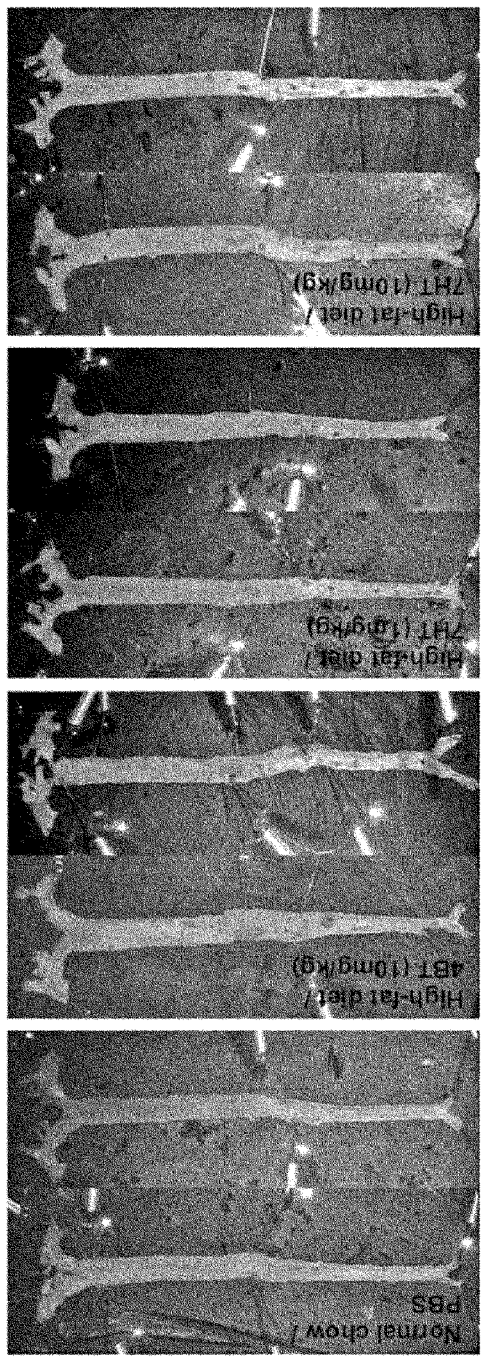
FIG. 20 is a graph showing the result of En face method to analyze atherosclerotic plaque formed in the artery according to one embodiment of the present invention.
Figure 21:
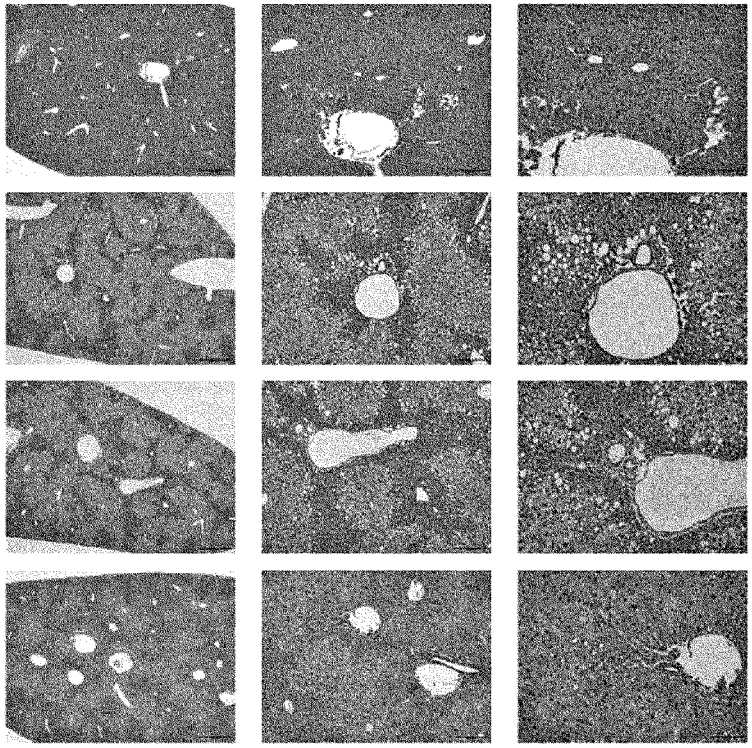
FIG. 21 is the result of pathological analysis of liver section by H&E staining in order to test toxicity of VCAM-1 antibody injection according to one embodiment of the present invention.
Figure 22:
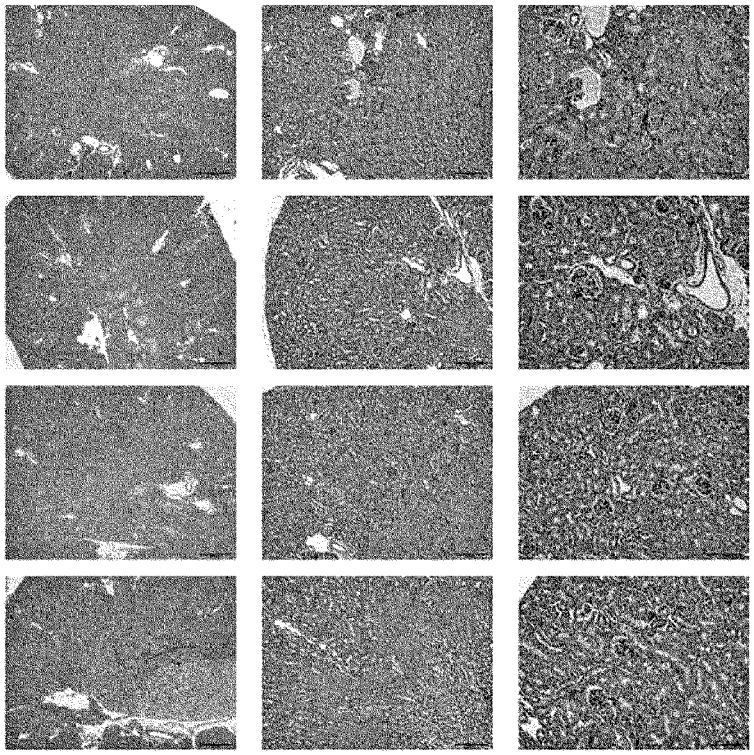
FIG. 22 is the result of pathological analysis of kidney section by H&E staining in order to test toxicity of VCAM-1 antibody injection according to one embodiment of the present invention.

Further, it was confirmed that adhesion and transmigration of inflammatory cells were effectively inhibited, when VCAM-1-expressing mouse arterial endothelial cells were treated with VCAM-1 antibody (7HT). Thereafter, it was also confirmed that VCAM-1 antibodies (7HT) specifically bind to arterial endothelial cells upon intraperitoneal injection of the antibodies into high-fat diet-fed mouse (FIG. 11). To investigate the therapeutic effect of VCAM-1 antibody (7HT) on cardiovascular disease, ApoE–/– mice were divided into four groups. Group 1 was administered with PBS and fed with normal chow diet twice a week, Group 2 was administered with a control antibody, 4BT (10 mg/kg) and fed with a high-fat diet twice a week, Group 3 was administered with the VCAM-1 antibody, 7HT (low dose of 1 mg/kg) and fed with a high-fat diet twice a week, and Group 4 was administered with the VCAM-1 antibody, 7HT (high dose of 10 mg/kg) and fed with a high-fat diet twice a week for 12 weeks. Then, an en-face technique for aortic lesions was performed to analyze arteriosclerosis, and a significant reduction in arteriosclerosis was found in Group 4, compared to Group 2 (FIGS. 17 and 18). In addition, frozen cardiac sections were sequentially prepared and analyzed to observe arteriosclerosis formed in the aortic arch. Consequently, a reduction in arteriosclerosis was found in Groups 3 and 4 (FIGS. 19 to 21). By hematologic analysis, it was confirmed that the result was not attributed to cholesterol metabolism/excretion (FIG. 15). There was no significant difference in the body weight and the amount of feed consumed during the experimental period (FIG. 14). After the experiment, a toxicity test was performed to examine the liver toxicity of the antibody (FIG. 15). It was confirmed that VCAM-1 antibody (7HT) inhibits VCAM-1 function, leading to alleviation of arteriosclerosis.

Accordingly, since the human recombinant monoclonal antibody of the present invention has a strong affinity to VCAM-1 expressed on human endothelial cells, it can be employed in any application requiring the VCAM-1 antigen recognition. In particular, it effectively inhibits adhesion and transmigration of leukocytes to the activated endothelial cells, thereby providing an effective diagnostic and therapeutic method for VCAM-1-mediated diseases such as inflammatory disease, cardiovascular disease and cancer.

Accordingly, in accordance with another embodiment, the present invention provides a method of providing information for the diagnosis of inflammatory disease, cardiovascular disease or cancer, comprising the step of detecting antigen-antibody reaction between the human recombinant monoclonal antibody and VCAM-1 in a biological sample of a subject suspected of having inflammatory disease or cancer, and a diagnostic composition for inflammatory disease, cardiovascular disease or cancer.

That is, a diagnostic composition comprising the monoclonal antibody that specifically binds to human VCAM-1 can be used to diagnose VCAM-1 expressionrelated diseases or VCAM-1-mediated diseases, for example, inflammatory disease, cardiovascular disease, or cancer.

The inflammatory disease may be selected from the group consisting of tumor necrosis factor-alpha (TNF-$\alpha$) mediated diseases and intestinal diseases, but is not limited thereto. Preferably, the tumor necrosis factor-alpha (TNF-$\alpha$) mediated diseases may be selected from the group consisting of asthma, diabetes, uveitis, ankylosing spondylitis, sepsis, endotoxin shock, hemodynamic shock, sepsis syndrome, ischemic reperfusion injury, malaria infection, mycobacterial infection, meningitis, psoriasis, congestive heart failure, fibrotic diseases, Kachexie, transplant rejection, autoimmune diseases, AIDS-related opportunistic infection, arthritis, rheumatoid spondylitis, gout, ankylosing gout, Crohn's disease, ulcerative trigonitis, multiple sclerosis, erythema nodosum leprosum (ENL), radiation injury, and hyperoxia-induced alveolar damage.

Further, the cardiovascular disease may be selected from the group consisting of myocardial infarction, heart attack, stroke, arrhythmia, hypertension, hyperlipemia and arteriosclerosis.

Further, the cancer may be selected from the group consisting of brain and spinal tumor, head and neck cancer, lung cancer, breast cancer, thymoma, mesothelioma, esophageal cancer, stomach cancer, colon cancer, liver cancer, pancreatic cancer, gallbladder cancer, renal cancer, prostate cancer, testicular cancer, germ cell tumor, ovarian cancer, cervical cancer, endometrial cancer, lymphoma, acute leukemia, chronic leukemia, multiple myeloma, sarcoma, malignant melanoma, and skin cancer.

Further, the diagnostic composition may include the human recombinant monoclonal antibody according to the present invention.

As used herein, the term "biological sample" may be a tissue, a cell, whole blood, serum, plasmic fluid, autoptical sample of tissue (brain, skin, lymph node, spinal cord), supernatant of cell culture, disruptive eukaryotic cell and bacterial expression system, but is not limited thereto. Existence of VCAM-1 or VCAM-1-associated disease can be detected by reacting manipulated or non-manipulated biological sample with the antibody of the present invention.

As used herein, the term "antigen-antibody complex" refers to a combination material of VCAM-1 antigen in the sample and the monoclonal antibody of the present invention that recognizes the antigen. Formation of such antigen-antibody complex may be detected by any method selected from a group consisting of colormetric method, electrochemical method, fluorimetric method, luminometry, particle counting method, visual assessment and scintillation counting method. However, the method is not limited to the above examples and has a variety of applications.

In the present invention, various labels may be used for detecting an antigen-antibody complex. Specific examples thereof may be selected from the group consisting of enzymes, fluorescent substances, ligands, luminescent substances, microparticles, and radioactive isotopes, but are not limited thereto.

Suitable examples of materials to be used as a label include acetylcholine esterase, alkaline phosphatase, β-D-galactosidase, horseradish peroxidase and β-lactamase as an enzyme; fluorescein, Eu3+, Eu3+ chelate and cryptate as a fluorescent; biotin-derivatives as a ligand; acridinium ester, isoluminol derivatives as a luminescent; colloidal gold, colored latex as a microparticle; and 57Co, 3H, 125I, 125I-Bonton Hunter reagent as a radioactive isotopes.

Preferably, the antigen-antibody complex may be detected by using Enzyme-linked immunosorbent assay (ELISA). ELISA techniques include a direct ELISA using a labeled antibody which recognizes an antigen adhered to a support body; an indirect ELISA using a labeled secondary antibody which recognizes a captured antibody of an antigen-antibody complex wherein the antigen adhered to a support body; a direct sandwich ELISA using another labeled antibody which recognizes an antigen of an antigen-antibody complex adhered to a support body; and an indirect sandwich ELISA using another labeled secondary antibody which recognizes an antibody, after reacting with the antibody which recognizes an antigen of an antigen-antibody complex adhered to a support body. The monoclonal antibody may have a detectable label, otherwise the antigen-antibody complex may be detected by treating another antibody which can capture the monoclonal antibody and has a detectable label.

The human recombinant monoclonal antibody of the present invention, which specifically binds to human VCAM-1, may be used alone or in the form of a pharmaceutical composition for preventing and treating inflammatory disease, cardiovascular disease or cancer, together with a conventional carrier.

Therefore, in still another embodiment, the present invention provides a prophylactic or therapeutic composition for inflammatory disease, cardiovascular disease or cancer, comprising the human recombinant monoclonal antibody and a pharmaceutically acceptable carrier, and a method for treating inflammatory disease, cardiovascular disease or cancer, comprising the step of administering the composition to a subject.

As used herein, the term "subject" encompasses horses, dogs, cats, pigs, goats, rabbits, hamsters, monkeys, guinea pigs, rats, mice, lizards, snakes, sheep, cattle, fish and birds, and means any animal (e.g., human).

As used herein, the term "prevention" means all of the actions in which the occurrence of the disease is restrained or retarded by the administration of the composition comprising the human recombinant monoclonal antibody according to the present invention and a pharmaceutically acceptable carrier.

As used herein, the term "treatment" means all of the actions in which the disease has taken a turn for the better or been modified favorably by the administration of the composition comprising the human recombinant monoclonal antibody according to the present invention and a pharmaceutically acceptable carrier.

The human recombinant monoclonal antibody of the present invention may also be used in combination with other antibodies, bioactive agents or materials for various purposes. For example, the human recombinant monoclonal antibody of the present invention may be used in combination with other anti-VCAM-1 antibodies in the treatment of disorders characterized by VCAM-1 expression in endothelium. Alternatively, the human recombinant monoclonal antibody of the present invention may be used in combination with antibodies recognizing other endothelial cell receptors identified in inflammatory events (e.g., ELAM1, ICAM1, etc.) and the known therapeutic drugs for inflammatory disease.

The inflammatory disease may be selected from the group consisting of tumor necrosis factor-alpha (TNF-α-mediated diseases and intestinal diseases, but is not limited thereto. Preferably, the tumor necrosis factor-alpha (TNF-α-mediated diseases may be selected from the group consisting of asthma, diabetes, uveitis, ankylosing spondylitis, sepsis, endotoxin shock, hemodynamic shock, sepsis syndrome, ischemic reperfusion injury, malaria infection, mycobacterial infection, meningitis, psoriasis, congestive heart failure, fibrotic diseases, Kachexie, transplant rejection, autoimmune diseases, AIDS-related opportunistic infection, arthritis, rheumatoid spondylitis, gout, ankylosing gout, Crohn's disease, ulcerative trigonitis, multiple sclerosis, erythema nodosum leprosum (ENL), radiation injury, and hyperoxia-induced alveolar damage.

Further, the cardiovascular disease may be selected from the group consisting of myocardial infarction, heart attack, stroke, arrhythmia, hypertension, hyperlipemia and arteriosclerosis.

Further, the cancer may be selected from the group consisting of brain and spinal tumor, head and neck cancer, lung cancer, breast cancer, thymoma, mesothelioma, esophageal cancer, stomach cancer, colon cancer, liver cancer, pancreatic cancer, gallbladder cancer, renal cancer, prostate cancer, testicular cancer, germ cell tumor, ovarian cancer, cervical cancer, endometrial cancer, lymphoma, acute leukemia, chronic leukemia, multiple myeloma, sarcoma, malignant melanoma, and skin cancer.

The composition comprising the human recombinant monoclonal antibody of the present invention may be administered in single or multiple doses in a pharmaceutically effective amount. In this regard, the composition may be administered in a form of solutions, powders, aerosols, capsules, enteric-coated tablets or capsules or suppositories. A variety of modes of administration are contemplated, including intraperitoneally, intravenously, intramuscularly, subcutaneously, intradermally, orally, topically, intranasally, intrapulmonarily and intrarectally, but the present invention is not limited to these exemplified modes of administration. However, since peptides are digested upon oral administration, active ingredients of a composition for oral administration should be coated or formulated for protection against degradation in the stomach.

In addition, the pharmaceutical composition may be administered using a certain apparatus capable of transporting the active ingredients into a target cell.

The composition comprising the human recombinant monoclonal antibody of the present invention may be administered in a pharmaceutically effective amount. The "pharmaceutically effective amount" refers to an amount sufficient for preventing or treating disease in a reasonable ratio of advantage/risk, which can be applicable to medical treatment or prevention. The level of the effective dosage can be determined according to the severity of the disease; drug activity; the age, weight, health, and sex of a patient; the drug sensitivity in a patient; the administration time, route, and release rate; the treatment duration; or elements including drugs that are blended or simultaneously used with the composition of the present invention, or other elements well-known in the medical field. In addition, the composition comprising the monoclonal antibody of the present invention may be administered singly or in combination with other therapeutic agents, or may be also administered with conventional therapeutic agents in a sequential or simultaneous manner.

In case of administrating the pharmaceutical composition of the present invention in a pharmaceutically effective amount, the human recombinant monoclonal antibody of the present invention, which has a strong affinity to VCAM-1, specifically binds to VCAM-1 expressed on endothelial cells and results in neutralization of VCAM-1. Ultimately, the human recombinant monoclonal antibody of the present invention inhibits the adhesion of leukocytes to leukocytes and transmigration of leukocytes through the endothelial cells, thereby treating inflammatory disease, cardiovascular disease and cancer. The inflammatory disease may be selected from the group consisting of tumor necrosis factor-alpha (TNF-α-mediated diseases and intestinal diseases, but is not limited thereto. Preferably, the tumor necrosis factor-alpha (TNF-α-mediated diseases may be selected from the group consisting of asthma, diabetes, uveitis, ankylosing spondylitis, sepsis, endotoxin shock, hemodynamic shock, sepsis syndrome, ischemic reperfusion injury, malaria infection, mycobacterial infection, meningitis, psoriasis, congestive heart failure, fibrotic diseases, Kachexie, transplant rejection, autoimmune diseases, AIDS-related opportunistic infection, arthritis, rheumatoid spondylitis, gout, ankylosing gout, Crohn's disease, ulcerative trigonitis, multiple sclerosis, erythema nodosum leprosum (ENL), radiation injury, and hyperoxia-induced alveolar damage.

Further, the cardiovascular disease may be selected from the group consisting of myocardial infarction, heart attack, stroke, arrhythmia, hypertension, hyperlipemia and arteriosclerosis.

Further, the cancer may be selected from the group consisting of brain and spinal tumor, head and neck cancer, lung cancer, breast cancer, thymoma, mesothelioma, esophageal cancer, stomach cancer, colon cancer, liver cancer, pancreatic cancer, gallbladder cancer, renal cancer, prostate cancer, testicular cancer, germ cell tumor, ovarian cancer, cervical cancer, endometrial cancer, lymphoma, acute leukemia, chronic leukemia, multiple myeloma, sarcoma, malignant melanoma, and skin cancer.

Further, in accordance with still another aspect, the present invention provide a method of inhibiting adhesion between leukocytes and activated endothelial cells and transmigration of leukocytes through the activated endothelial cells using the human recombinant monoclonal antibody according to the present invention. That is, VCAM-1 binds to VLA-4(very late antigen-4) and α4β1 integrin that are expressed on activated leukocytes in inflammation and immune rejection, and plays a critical role in promoting the interaction between endothelial cells and leukocytes including monocyte and T cells. The monoclonal antibody according to the present invention specifically binds to VCAM-1, thereby inhibiting adhesion between leukocytes and activated endothelial cells and transmigration of leukocytes through the activated endothelial cells.

Various publications are cited herein which are hereby incorporated, by reference, in their entireties. Through the conventional experiments, those skilled in the art will recognize or appreciate that numerous equivalent embodiments are contemplated herein. Such equivalents are therefore intended to be embraced by the claims.

Mode for the Invention

Hereinafter, the present invention will be described in more detail with reference to Examples. However, the following Examples are provided only for the purpose of illustrating the present invention, and accordingly it is not intended that the present invention is limited thereto.

1. Preparation of Human and Mouse VCAM-1 Antigen 1.1. Cloning of Human VCAM-1

A plasmid containing human VCAM-1 gene (hMU012650) (Kugi # IRAU-75-G02) was purchased from KUGI (Korean UniGene Information) provided by Center for Functional Analysis of Human Genome, Korea Research Institute of Bioscience and Biotechnology (KRIBB). The plasmid was used as a template DNA, and in order to express only D1-D2 domain and D1-D4 domain of VCAM-1, each gene was amplified using a forward primer (5'-CAGGGGGC-CGTGGGGGCCTTTAAAATCGAGACCACCCC-3')(SEQ ID NO: 17) and a reverse primer (5'-TAGCGGCCGACGCG-GCCAATTGCAATTCTTTTACAGCCTG-3')(SEQ ID NO: 18) for D1-D2 domain of VCAM-1, and a forward primer (5'-CAGGGGGCCGTGGGGGCCTTTAAAATC-GAGACCACCCC-3')(SEQ ID NO: 19) and a reverse primer (5'-TAGCGGCCGACGCGGCCAAGAGCTCCAC-CTGGATTCCCT-3')(SEQ ID NO: 20) for D1-D4 domain of VCAM-1. After treatment of sfiI, ligase was used to clone the genes into a pYK602-Fc vector and a pYK602-His only vector (vector constructed by KRIBB), respectively. PCR products were obtained under the following PCR conditions: for a total reaction volume of 50 ul, a template of 100 ng was reacted at 94° C. for 2 min, and then at 94° C. for 30 sec, at 55° C. for 30 sec, and at 72° C. for 1min and 30 sec (D1-D4), and 45 sec (D1-D2) for 30 cycles, and then 10 min at 72° C. Moreover, base sequences of the cloned pYK602-FC-VCAM-1-D1-D2, pYK602-His-VCAM-1-D1-D2, pYK602-FC-VCAM-1-D1-D4, and pYK602-His-VCAM-1-D1-D4 vectors were examined.

1.2. Expression and Purification of VCAM-1 Protein

Among various proteins, the entire molecule-containing hVCAM-Fc-chimera (R&D system, cat#: 862-VC) and mVCAM-1-Fc chimera (R&D systems, Cat#: 643-VM) were commercially purchased, and expression and purification of the fragments with each VCAM-1 domain were performed as follows.

First, $5 \times 10^6$ 293E cells were plated in 10 dishes of 150 mm diameter, and on next day, each 20 μg of the cloned pYK602-VCAM-1-D1-D2 vector and pYK602-VCAM-1-D1-D4 vector were treated with PEI (23966: Polysciences, Inc, USA) for transfection. Next day, the media was replaced with serum-free DMEM, and then the supernatants were collected every other day, followed by electrophoresis in a 10% SDS-PAGE gel and Western blotting for analysis of expression level.

The supernatants, in which the expression of hVCAM-1-D1-D2-Fc and hVCAM-1-D1-D4-Fc was confirmed, were collected, and filtered using a 0.22 μm Top-filter (Millipore, Cat#: SCGP T05 RE) to obtain a sufficient amount of protein. The proteins were purified before use, as follows. First, an Econo-column (Bio-Rad Cat. No 737-1006, 1×5 cm) was washed with PBS, and packed with 500 μl of protein A (Amersham Cat. No. 17-1279-30). During performing the packing, 10 ml of PBS (pH 7.4) was applied to the column to wash beads, and 30 ml of 20 mM sodium phosphate buffer (pH 7.0) was applied as a binding buffer. Subsequently, the obtained supernatant was applied thereto using a Peri-staltic pump (Bio-Rad Cat. No. 731-8142) at a flow rate of 0.5 ml/min. After binding to the column, it was washed with PBS at a flow rate of 2 ml/min for 1 hr, followed by elution. 500 μl of 0.1 M glycine-HCl (pH 2.5) was used for elution, and ⅒ volume of 1 M Tris-HCl (pH 9.0) was added for neutralization. Among 6 elution fractions, the protein was mainly eluted in #1 and #2 fractions. These two fractions were put in 10 K dialysis membrane, followed by o/n dialysis in 4 L of PBS. All the above processes were performed in a 4° C. cold room. After quantification, the products were aliquoted and stored at −70° C. After purification, the products were confirmed on 10% SDS-PAGE gel. hVCAM-1-D1-D2-Fc and hVCAM-1-D1-D4-Fc were obtained in an amount of 2.8 mg and 800 μg, respectively. The supernatants, in which the expression of hVCAM-1-D1-D2-his and hVCAM-1-D1-D4-his was confirmed, were collected, filtered using a 0.22 μm Top-filter (Millipore, Cat#: SCGP T05 RE) and concentrated using pellicon XL membrane (Millipore, 8K, cat #: PXB0 08A 50) of LabScale TFF System (Millipore, Cat#: XX42LSS11) to ⅒ volume. 10-fold volume of an IMAC buffer solution (300 mM KCl, 50 mM KH2PO4, 5 mM imidazole, pH 8.0) was added to the concentrate, and replaced by the IMAC buffer solution. Purification was performed using a Bio-Scale Mini profinity IMAC cartridge (cat#: 732-4610) of Profinia™ protein Purification System (Bio-Rad) at a rate of 1 ml/min according to the manufacturer's instructions. The eluent was dialyzed using a membrane (10K, 132574:SPECTRAPOR, USA) in 4 L of PBS solution at 4° C. for 4 hr or longer, and then dialyzed again in 4 L of precooled PBS solution overnight. After o/n dialysis, the resultant was transferred to an e-tube, and protein concentration was determined by the Bradford method. Consequently, 400 μg of hVCAM-1-D1-D4-his and hVCAM-1-D1-D2-Fc proteins were obtained, and examined in a 10% SDS-PAGE gel.

2. Construction of Library Phage $2.7 \times 10^{10}$ human scFv library cells having diversity were cultured in SB medium [30 g of bactotrypton, 20 g of Yeast extract, 10 g of MOPS, pH 7.0] containing 50 μg/ml ampicillin and 2% glucose at 37° C. for 2-3 hrs (OD600=0.5). Then, the cells were infected with VCSM13 helper phage, followed by culture in a medium containing 70 μg/ml kanamycin and 1 mM IPTG at 30° C. for 16 hrs. The cells proceeded to centrifugation (4500 rpm, 15 min, 4° C.) and supernatant was obtained, which was dissolved in a solution supplemented with 4% PEG 6000 and 3% NaCl, followed by reaction in ice for 1 hr. The reactant was centrifuged again (8000 rpm, 20 min, 4° C.). The pellet was dissolved in PBS, which proceeded to centrifugation again (12000 rpm, 10 min, 4° C.). As a result, the supernatant containing library phage was obtained, which was transferred into a new tube and stored at 4° C.

3. Biopanning by Phage Display

When VCAM-1 consisting of seven IgG-like domains binds with its ligand, alpha4beta1 integrin (α4β1 integrin), its domains 1 and 4 are known to function as a binding motif. Thus, panning was performed using human VCAM-1-D1-D4 (hVCAM-1-D1-D4) as well as the entire VCAM-1 molecule. In this Example, the panning method and result for hVCAM-1-D1-D4 will be described.

3.1. Biopanning on hVCAM-1-D1-D2 and hVCAM-1-D1-D4 Antigens

An immunosorb tube (Nunc 470319) coated with 10 μg/ml human recombinant VACM-1 (R&D system, 809-VR) antigen was first blocked with skim milk/PBS, and cultured with the prepared library phage ($1 \times 10^{12}$ cfu) at room temperature for 1-2 hrs. The tube was washed with TBST (0.05%) three times. Bound phages were eluted with 1 ml of fresh 100 mM triethylamine solution at room temperature for 10 min. The eluted phages were neutralized with 1 M Tris (pH 7.4), and infected into E. coli (ER2537), and cultured at 37° C. for 1 hr. The infected E. coli was plated onto LB-agarose media plate (diameter 15 cm) containing 2% glucose and ampicillin, and cultured at 37° C. for 16 hr. The cultured E. coli was dispersed in 5 mL of SB, and 50 ml thereof was inoculated in 20 ml of SB-ampicillin-glucose to obtain a solution containing bound phages according to the method of <1. Construction of Library Phage>, and then used in the next round of panning. For 2nd-4th pannings after 1st panning, the immunosorb tube was coated with each of hVCAM-1-D1-D2 and hVCAM-1-D1-D4 antigens, and each panning was performed (see Table 1).

TABLE 1

Result of Panning by hVCAM-1-D1-D2 and hVCAM-1-D1-D4 antigens

| Panning round | D1-D2 input | D1-D2 output | D1-D4 input | D1-D4 output |
|---|---|---|---|---|
| 1st (*) | $2.2 \times 10^{11}$ | $2.5 \times 10^{8}$ | $2.2 \times 10^{11}$ | $2.5 \times 10^{8}$ |
| 2nd | $1.5 \times 10^{12}$ | $2.5 \times 10^{8}$ | $1.5 \times 10^{12}$ | $2.5 \times 10^{8}$ |
| 3rd | $1.2 \times 10^{12}$ | $5 \times 10^{7}$ | $5 \times 10^{11}$ | n/d |
| 4th | $1.5 \times 10^{12}$ | $5 \times 10^{7}$ | $2.0 \times 10^{12}$ | $5 \times 10^{17}$ |

(*) recombinant VACM-1 (R&D system, 809-VR) was commonly used as an antigen of 1st panning.

3.2. Screening of Monoclonal Antibody Against hVCAM-1-D1-D4 Antigen

After 4th round of panning, each of single colonies was picked from an output titer plate using a sterile toothpick, and inoculated in a 96-well plate containing SB-ampicillin media (200 µl/well), followed by incubation at 37° C. for 2~3 hrs (OD600=0.5~0.7). Subsequently, 20 µl of 10 mM IPTG was added to each well, and cultured at 30° C. for 16 hrs. Each well of 96-well immunoplate (Costar 3690) was coated with 250 ng of hVCAM-1-D1-D4 antigen using a coating buffer solution at 37° C. for 1 hr, and then blocked with skim milk (3%) in PBS. The scFv phages of 4th round of panning were first centrifuged (3000 rpm, 15 min), and the supernatant was removed. 60 µl of TES buffer was added to each well, followed by incubation in ice for 30 min. Thereafter, centrifugation (3000 rpm, 15 min) was performed, and 25 µl of each supernatant was added to each well of 96-well immunoplate coated with VCAM-1-D1-D4 antigen, from which 3% skim milk/PBS was removed.

Each well was washed with 0.2 ml of PBS-tween 20 (0.05%) four times, and then treated with 25 µl of secondary antibody anti-HA-HRP (Santan Cruz, SC-7392) diluted in 3% skim milk/PBS at a ratio of 1:3000, followed by incubation for 1 hr. Each well was washed with 0.2 ml of PBS-tween 20 (0.05%) four times, and treated with 25 µl of TMB solution, and left for 5 min. After reaction, 25 µl of 1 M H2SO4 was immediately added to each well to terminate the reaction, and absorbance at 450 nm was measured using a Spectrophotometer (MolecularDevice, USA).

As a result, binding capacities of 78 single phage clones to hVCAM-1-D1-D4 antigen were compared, and their types were confirmed by finger printing and sequence analysis. Finally, 20 different types of phage antibodies were selected.

4. Cloning of Full IgG Form

To convert the monoclonal phage antibodies against hVCAM-1 from phage to full IgG vector, colony PCR (iCycler iQ, BIO-RAD) was performed to obtain a heavy chain using 1 µl of monoclone DNA and 10 pmole/µl of a heavy chain forward primer and a heavy chain reverse primer, 5 µl of 10× buffer, 1 µl of 10 mM dNTP mix, 0.5 µl of pfu DNA polymerase (Solgent, co., 2.5 U/µl), and distilled water. In addition, colony PCR was also performed to obtain a light chain using light chain forward and reverse primers in the same manner.

The heavy chain DNAs obtained from PCR were purified using a DNA-gel extraction kit (Qiagen), and mixed with 1 ul of pNATAB H vector (10 ng), 15 ul of heavy chain(100~200 ng), 2 ul of 10×Buffer, 1 ul of ligase (1 U/ul), and distilled water, left at room temperature for 1~2 hrs for ligation with the vector. Competent cells (XL1-blue) were added thereto, and left in ice for 30 min, followed by heat-shock at 42° C. for 90 sec for transformation. The mixture was placed in ice again for 5 min, and 1 Ml of LB medium was added thereto. After incubation at 37° C. for 1 hr, the cells were spread on LB Amp solid medium, followed by incubation at 37° C. for 16 hrs. The single colony obtained was inoculated in 5 Ml of LB Amp liquid medium, followed by incubation at 37° C. for 16 hrs. DNA was extracted from the culture medium using a DNA-prep. Kit (Nuclogen). The light chain DNA was also extracted using a pNATAB L vector in the same manner as the above. Sequencing analysis of the obtained DNA was performed using a CMVproF primer (AAA TGG GCG GTA GGC GTG) (SEQ ID NO: 29) (Solgent). As a result, it was confirmed that the heavy chain and the light chain sequences of full IgG converted from 9 clones against VCAM-1 were identical to the sequence of phage antibody.

5. Transient Gene Expression of Antibody

Transient gene expression from the cloned full IgG heavy chain and light chain DNAs was performed.

CHO (Chinese Hamster Ovary)-S was used as a host cell for transient gene expression to induce transfection in a mixed solution of Opti-MEMI (GIBCO 31985, Invitrogen) with lipofectamine 2000 (Cat no. 11668-019, Invitrogen) and DNA (1:1). To maximize the transient expression, heavy chain and light chain DNAs were used at a ratio of 1:1. RPMI 1640 medium (GIBCO 22400, Invitrogen) was used for transfection, and the cell was used at a concentration of 2×106 cells/ml. After the mixed solution was reacted for 20 min, and mixed with the transfection medium at a ratio of 1:9, followed by incubation in a 5% CO2 37° C. shaking incubator at 110 rpm for 4 hrs. Subsequently, CD-CHO medium (GIBCO 10743, Invitrogen) containing 8 mM glutamine (GIBCO 25030, L-Glutamine 200 mM, 100×, Invitrogen) and HTS (GIBCO, HT Supplement, Cat no. 11067-030, Invitrogen) was added thereto in an equal volume of the transfection medium. The flask was incubated in an 8% CO2 37° C. shaking incubator at 100 rpm for 4 days. The cultured sample was centrifuged at 8,000 g for 15 min to remove cell debris, and the supernatant was filtered using a 0.22 µm filter (Corning) to prepare a culture solution for isolation and purification of antibody.

6. Isolation and Purification of Antibody

The supernatant prepared in Example 5 was passed through a recombinant protein-A sepharose column (Hitrap rProteinA FF, 5 mL, GE healthcare) equilibrated using an equilibrium buffer (50 mM Tris-HCl (pH 7.4), 100 mM NaCl). The antibodies binding to the column was eluted with 0.1 M Na-citrate (pH 3.0), 100 mM NaCl solution, and neutralized with 1 M Tris-HCl (pH 9.0), followed by dialysis in a PBS (phosphate buffered saline, pH 7.4, Welgene) buffer solution. The purified antibody was electrophoresed on Bis-Tris 4-12% gradient SDS-polyacrylamide gel (NuPAGE gel, Invitrogen) under reduced conditions. As a result, about 55 kDa of heavy chain and about 25 kDa of light chain were detected.

7. Analysis of Antigen Affinity of Antibody

7.1. Affinity to Antigen Domain

The location of anti VCAM-1 antibody-binding region in VCAM-1 consisting of seven domains was identified by ELISA. Each well of microplate was coated with a recombinant human VCAM-1 domain 1~2/Fc chimera (hereinbelow, referred to as 'VD2', A&R therapeutics), VCAM-1 domain 1~4/Fc chimera (hereinbelow, referred to as 'VD4', A&R therapeutics), and VCAM-1 domain 1-7/Fc chimera (hereinbelow, referred to as 'VD7', R&D, 862-VC) at a concentration of 2 µg/ml at 4° C. overnight. The plate was washed using PBS once, and blocked using PBS supplemented with 3% BSA (bovine serum albumin) at 37° C. for 2 hrs, followed by incubation in cell culture medium containing 7H antibody (1:50) at 37° C. for 2 hrs. The plate was washed with PBS containing 0.05% Tween 20 four times, and the amount of anti VCAM-1 antibody binding to recombinant human VCAM-1 antigen was detected by anti-Fab monoclonal antibody horseradish peroxidase-conjugated anti-F(ab')2 antibody. The plate was reacted with a TMB substrate solution (3,3,5,5-Tetramethylbenzidine) at room temperature for about 5 min, and the reaction was terminated by 1 N (normal) sulfuric acid solution to measure optical density at 450 nm. With respect to H6 antibody, the purified antibody was diluted to 100~125 ng/ml, and reacted, and then detected by the action of horseradish peroxidase-conjugated anti-kappa light chain antibody.

As shown in FIG. 2, it was found that H6 had a strong binding capacity to all VCAM-1 domains, 1-2 (VD2), 1-4

(VD4), and 1-7 (VD7). In particular, H6 antibody was found to have an excellent binding capacity to 1-2 domain (VD2) among 7 domains of VCAM-1. 7H antibody was also found to have an excellent binding capacity to 1-2 domain (VD2) among the VCAM-1 domains.

7.2. Affinity Analysis by BIACORE

In order to determine the binding affinity of anti VCAM-1 antibodies, H6 and 7HT to human VCAM-1 antigen, each antigen as a ligand was immobilized to a sensor chip (Sensor chip CM5, BIACORE, BR-1003-99), and then each dilution of the human antibodies was applied to the immobilized ligand using BIACORE to induce association and dissociation between antigen and antibody, thereby determining the association/dissociation constant Kd value, which indicates a binding interaction between the corresponding antigen and antibody. The results are shown in FIG. 3 (Reference: Thomas Hofer, Wisit Tangkeangsirisin, Michael G. Kennedy, Rose G. Mage, Stephen J. Raiker, Karthik Venkatesh, Hakjoo Lee, Roman J. Giger, Christoph Rader Chimeric rabbit/human Fab and IgG specific for members of the Nogo-66 receptor family selected for species cross-reactivity with an improved phage display vector Journal of Immunological Methods 318 (2007) 75.87; Paula Gomes a, David Andreu Direct kinetic assay of interactions between small peptides and immobilized antibodies using a surface plasmon resonance biosensor Journal of Immunological Methods 259, 2002.217-230, and Kikuchi Y, Uno S, Nanami M, Yoshimura Y, Lida S, Fukushima N, Tsuchiya M. Determination of concentration and binding affinity of antibody fragments by use of surface plasmon resonance. Journal of Bioscience and Bioengineering Vol. 100, No. 3, 311-317, 2005).

BIACORE analysis comprises the three steps of 1) Pre-concentration that determines coupling conditions between sensor chip and ligand; 2) immobilization of ligand to sensor chip; and 3) binding of analyte to the immobilized ligand.

1) Pre-concentration

In this experiment, a conventional BIACORE sensor chip CM5 (BIACORE, BR-1003-99) was used, and before ligand immobilization to the chip, the electrostatic attraction of ligand to the sensor surface was determined via change in pH 4.0-5.5 of sodium acetate, which is used as a coupling buffer.

2) Ligand Immobilization

For ligand immobilization to the sensor chip CM5, the chip should be first activated with a mixture of N-hydroxysuccinimide (NHS) and Nethyl-n'-(dimethylaminopropyl) (EDC) (Amine Coupling Kit, BR-1000-50) to prepare a NHS-ester-activated chip surface being highly reactive to amino group. 1 mg/ml of ligand to be immobilized was diluted in 97 µl of each sodium acetate solution (vary within the pH range from 4.0 to 5.5) at a dilution ratio of 3/100, and then applied at a flow rate of 10 µl/min for about 3 min (as a negative control, the ligand was diluted using a running buffer, HBS-EP buffer (BIACORE AB, Sweden) in the same manner). In order to immobilize the ligand at a predetermined value target RU (resonance unit), serial injection was carried out automatically, until reaching target RU. The ligandimmobilized chip was inactivated by injection of 1 M ethanolamine (Amine Coupling Kit, BR-1000-50) at a flow rate of 10 µl/min for about 3 min. The final RU was determined by an immobilization report which provides a difference in RU values before and after injection of ethanolamine.

3) Binding of Analyte to the Immobilized Ligand

A flow cell 2-flow cell 1 mode provided by BIACORE instrument was employed in this experiment in order to remove non-specific binding. At this time, a recombinant VCAM1/Fc antigen was immobilized as a ligand to the flow cell 2, and BSA (Bovine Serum Albumin) was immobilized to the flow cell 1. Then, anti VCAM-1 antibody H6 as the analyte were applied to flow cell 1 and 2, simultaneously. The sensogram RU of flow cell 1 was automatically subtracted from the sensogram RU of flow cell 2. Subsequently, the analytes were applied at a flow rate of 30 µl/min for about 3 min, and then dissociation was induced for 120 sec. Through this procedure, an association/dissociation curve of the corresponding antigen and antibody was obtained, and an association/dissociation constant KD was calculated by BIAevaluation program (BIACORE AB, Sweden), as shown in FIG. 3. As a result, it was found that H6 antibody against human VCAM-1 antigen has an excellent binding capacity of about 0.6 nM, and 7HT antibody has a binding capacity of about 6.3 nM.

8. Inhibitory Effect of Antibody on Leukocyte Adhesion 8.1. Inhibitory Effect on Adhesion Between Human VCAM-1 Antigen and Leukocyte Each well of 96-well plate (Maxisorp, Nunc) was coated with 100 µl of recombinant human VCAM-1 (10 µg/ml, Cat. No.: 809-VR-200, R&D systems) for 1 hr, and then H6 antibody was added to the VCAM-1-coated well in an amount of 0.01, 0.1, 1.0 and 10.0 µg for antigen binding for 1 hr. At this time, 4B2 mouse anti-human VCAM-1 monoclonal antibody (Cat. No.: BBA5, R&D) was used as a positive control, and as a negative control, the antigen was only treated without antibody. While binding of antibodies to the antigen, the fluorescence staining of human leukocyte cell U937 (Cat. No.: CRL-1593.2, ATCC) was performed using 5 µM of BCECF-AM (Cat. No.: 216254, Calbiochem). Next, U937 cell was treated with 100% human serum (Cat. No.: H4522, Sigma) to inactivate the Fc receptor on the cell surface. The leukocyte cells treated with fluorescence staining and Fc receptor inactivation were suspended to a density of $1.0 \times 10^6$ cells/ml in RPMI 1640 (Cat. No.: 22400-089, Invitrogen) supplemented with 1% fetal calf bovine serum. 100 µl of the prepared U937 cells were applied to each well of the antigen and antibody-treated plate, and incubated in a 37° C. 5% CO2 incubator for 15 min, and each well was filled with RPMI 1640 supplemented with 1% fetal calf bovine serum, and sealed tightly with a sealing tape. The plate was placed upside down, and centrifuged at 200×g force for 5 min. The sealing tape was removed from the upside-down centrifuged plate. The medium and unbound U937 cells were completely removed, and 150 µl of cell lysis buffer (50 mM Tris-HCl (pH8.5), 0.1% SDS) was added to each well to lyse the bound U937 cells for 15 min. Subsequently, the plate was placed in a fluorometer (GeminiX, Molecular Device), and fluorescence intensity was measured at an absorbance wavelength 485 nm/emission wavelength 530 nm. Mean values of the triplicate measurements (per each experimental condition) were calculated, and reduction in fluorescence intensity compared to that of non-antibody treated group was calculated to analyze the inhibition rate. As a result, H6 antibody showed 80% or higher inhibition at an amount of 1 µg or more (see FIG. 4).

8.2. Inhibitory Effect on Adhesion Between Human Endothelial Cell and Leukocyte $2 \times 10^4$ human endothelial cell HUVEC was plated on each well of 96-well plate (Microtest tissue culture 96-well plate, BD-Falcon), and cultured in EGM-2 media (Lonza) for about 3 days according to the manufacturer's instructions. When cell monolayer was observed under a microscope, the cells were stimulated with 20 ng/ml of human TNF-α for 24 hrs. Thereafter, to remove TNF-α, each well was washed with 200 µl of EGM-2 medium twice, and the antibody H6 was added to the HUVEC monolayer plated on the well in an amount of 0.01, 0.1, 1.0 and 10.0 µg, respectively. The plate was incubated for 1 hr to induce antigen-antibody binding. At this time, 0.5 and 5.0 μg of 4B2 mouse anti-human VCAM-1 monoclonal antibody (Cat. No.: BBA5, R&D) and mouse anti-α4 integrin antibody were used as a positive control, and as a negative control, the antigen was only treated without antibody. While binding of antibodies to the antigen, the fluorescence staining of human leukocyte cell U937 (Cat. No.: CRL-1593.2, ATCC) was performed using 5 μM of BCECF-AM (Cat. No.: 216254, Calbiochem). Next, U937 cell was treated with 100% human serum (Cat. No.: H4522, Sigma) to inactivate the Fc receptor on the cell surface. The U937 cells treated with fluorescence staining and Fc receptor inactivation were suspended to a density of $1.0 \times 10^6$ cells/ml in RPMI 1640 (Cat. No.: 22400-089, Invitrogen) supplemented with 1% fetal calf bovine serum. 100 μl of the prepared U937 cells were applied to each well of the antibody-treated HUVEC, and aluminium foil was used to block light. The plate was incubated in a 37° C. 5% CO2 incubator for 10 min, and placed upside down to remove the medium and unbound cells. Each well was filled with RPMI 1640 supplemented with 1% fetal bovine serum, and sealed tightly with a sealing tape. The upside-down plate was centrifuged at 400×g force for 5 min. The sealing tape was removed from the upside-down centrifuged plate. The medium and unbound U937 cells were completely removed, and 150 μl of cell lysis buffer (50 mM Tris-HCl (pH 8.5), 0.1% SDS) was added to each well to lyse the bound U937 cells for 15 min. Subsequently, the plate was placed in a fluorometer (GeminiX, Molecular Device), and fluorescence intensity was measured at an absorbance wavelength 485 nm/emission wavelength 530 nm. Mean values of the triplicate measurements (per each experimental condition) were calculated, and reduction in fluorescence intensity compared to that of non-antibody treated group was calculated to analyze the inhibition rate. As a result, H6 showed approximately 25~65% inhibition at an amount of 0.1 μg~10.0 μg (see FIG. 5). These results are similar to the analysis results of inhibitory effect on adhesion between VCAM-1 antigen and leukocyte in Example 8.1.

9. Inhibitory Effect on Permeability of Leukocyte to Human Endothelial Cell $2 \times 10^4$ cell/300 μl (EGM-2 media) of Human endothelial cells (human umbilical vein endothelial cell (HUVEC), Cambrex, C2517A) were cultured in an insert of transwell (6.5 mm insert, 5 um polycarbonate membrane, Corning, 3421) for about 4 days until monolayer formation. The cells were treated with human TNF-α (20 ng/ml, abcam, ab9642) that is a VCAM-1 expression-inducing factor, and VCAM-1 expression was induced for 14~16 hrs. HUVEC cells of passages 1~5 were used.

Human promonocytic leukocyte (U937, CRL-1593.2™) was washed with 1% FBS/RPMI 1640 (Gibco, 22400) medium twice (centrifugation at 1100 rpm for 3 min), and then suspended in human serum (Sigma, H4522) to a density of $5 \times 10^6$ cell/ml, followed by incubation at room temperature for 15 min for blocking Fc receptor. The media supplemented with TNF-α was removed from the insert with HUVEC, and antibody H6 was added to 100 ul of 1% FBS/RPMI media, and a portion of Fc receptor-blocked U937 cells was suspended in anti-alpha 4 integrin antibody or recombinant human VCAM-1 antigen, and pre-treated at 37° C. for 30 min. U937 cells in 1% FBS/RPMI media ($5 \times 10^5$ cell/200 μl) were added to the pre-treated HUVEC, and the equal number of U937 cells suspended in anti-alpha 4 integrin antibody was also added to HUVEC. At this time, to induce transendothelial migration of U937 leukocyte, 400 μl of 10 nM C5a (R&D, 2037C5) was added to each well, followed by incubation at 37° C. for 2~6 hrs. Thereafter, the insert was removed, and the leukocytes migrated to the bottom well were recovered in e-tube. Centrifugation was performed at 1,500 rpm for 3 min to remove media, and then the cell pellet was suspended in 600 μl of 1×PBS to count the number of cell (Cell counter, Beckman Coulter TM, Vi-Cell XR 2.03).

The number of non-specifically transmigrated leukocytes of the non-treated group (not treated with TNF-α and C5a) was subtracted from the number of transmigrated leukocytes through the TNF-α-treated HUVEC experimental group (Human IgG control-treated group) by treatment of C5a, which was regarded as 100% migration. Migration inhibition (%) of each antibody was calculated. As a result, H6 antibody was found to show approximately 25% migration inhibition (see FIG. 6).

10. Inhibitory Effect on RhoA (Ras Homolog Gene Family, Member A) Activity $2 \times 10^5$ HUVEC (Human Umbilical Vein Endothelial Cells) were inoculated in a 6-well plate, and cultured for about 3 days until monolayer formation. To remove serum present in the culture medium, the plate was washed with EBM-2 medium (Cat. No.: CC-3156, Lonza) once, and 20 ng/ml of human TNF-α ?diluted in EBM-2 medium supplemented with 0.25% fetal bovine serum was added to induce VCAM-1 expression for 14~16 hrs. After removing the culture medium, H6 antibody and control antibody (IgG4, Cat. No.: 14764, Sigma) were added at a concentration of 10 μg/ml, followed by incubation for 30 min at 37° C. 10 μg/ml of anti VCAM-1 antibody (Cat. No.: BBA5, BDR&D) used for cross-linking of VCAM-1 on the cell surface was added, followed by incubation for 30 min at 37° C. HRP-conjugated anti-mouse antibody (Cat. No.: A9917, Sigma) was added in a ratio of 1:100, followed by incubation for 15 min at 37° C. After the reaction was completed, the plate was immediately placed in ice and the medium was removed, and washed with cold PBS once. After the residual PBS was completely removed from the plate, 100 μl of a cell lysis buffer included in a RhoA activation kit (Cat. No.: BK124, Cytoskeleton) was added to each well, and the lysed cells were recovered. Subsequent procedures were carried out according to the manual in the kit, and repeated three times.

As a result, it was found that H6 antibody showed approximately 56% inhibition rate on the RhoA activity induced by cross-linking of VCAM-1 expressed on the cell surface.

11. Inhibitory Effect on ROS (Reactive Oxygen Species) Activity $2 \times 10^5$ HUVEC (Human Umbilical Vein Endothelial Cells) were inoculated in a 6-well plate, and cultured for about 3 days until monolayer formation. To remove serum present in the culture medium, the plate was washed with EBM-2 medium (Cat. No.: CC-3156, Lonza) once, and 20 ng/ml of human TNF-α diluted in EBM-2 medium supplemented with 0.25% fetal bovine serum was added to induce VCAM-1 expression for 14-16 hrs. After removing the culture medium and washing with EBM-2 medium twice, H6 antibody and control antibody (IgG4, Cat. No.: 14764, Sigma) were added at a concentration of 10 μg/ml, followed by incubation for 30 min at 37° C. After each well was washed with EBM-2 medium twice, 10 μg/ml of anti VCAM-1 antibody (Cat. No.: BBA5, R&D) used for cross-linking of VCAM-1 on the cell surface was added, followed by incubation for 30 min at 37° C. After each well was washed with EBM-2 medium twice, HRP-conjugated anti-mouse antibody (Cat. No.: A9917, Sigma) was added in a ratio of 1:100, followed by incubation for 30 min at 37° C. Each well was washed with EBM-2 medium twice. After the medium was completely removed, each well was treated with 150 μl of 10 μM DCF (2',7'-dichlorofluorescein diacetate) diluted in EBM-2 medium. Then, fluorescence (wavelength 495 nm-527 nm) was examined every 10 min for 3 hrs, and the effect of antibody was evaluated by the value measured at 3 hrs. The experiment was repeated three times.

As a result, it was found that H6 antibody showed approximately 33% inhibition rate on the ROS activity induced by cross-linking of VCAM-1 expressed on the cell surface.

12. Analysis of Internalization $2 \times 10^5$ HUVEC (Human Umbilical Vein Endothelial Cells) were inoculated in a 6-well plate, and cultured for about 3 days until monolayer formation. The cells were treated with human TNF-α (20 ng/ml, Cat. No.: ab9642, abcam) to induce VCAM-1 expression for 14~16 hrs. HUVEC of passages 1-5 was used. To remove human TNF-α, the cells were washed with PBS once, and the plate was left at 4° C. for 20 min. HUVEC was treated with H6 antibody diluted in PBS supplemented with 1% BSA (10 ug/ml), and incubated at 4° C. for 30 min to induce binding. Then, the cells were washed with PBS once. The plate was left at 37° C. for 2 min, 10 min, 30 min, and 60 min to induce internalization of VCAM-1-bound antibodies, followed by washing. Except the experiment group for VCAM-1 expression test, 1 ml of acidic PBS (pH 2.5) was added to each experiment group, and left at room temperature for 5 min to remove antibodies on the cell surface, followed by washing. The cells were recovered by trypsin treatment (Cat. No.: CC-5034, Clonetics), and reacted with 4% formaldehyde (in PBS) at room temperature for 10 min. The cells were washed with PBS once, and reacted with 0.2% Triton X-100 (in PBS) for 10 min, followed by washing with PBS once. FITC-conjugated goat anti-human IgG antibody (Cat. No.: F9512, Sigma) was added thereto, and binding was induced at 4° C. for 30 min. Then, the cells were washed with PBS once, and analyzed by Flow cytometry. The experiment was repeated twice.

As a result, apparent cell surface VCAM-1 expression (arrow, sky blue) was observed, compared to that of the isotype control (grey). In addition, when the induction of internalization was analyzed at each time point, internalization was initiated at 2 min and reached the maximum at 30 min after binding of antibody to VCAM-1.

13. Analysis of Inhibitory Effect of VCAM-1 Antibody on Inflammatory Cell Adhesion Via in Vitro Adhesion Assay To confirm whether VCAM-1 antibody binds to vascular endothelial cells to inhibit adhesion of inflammatory cells, arterial vascular endothelial cells of C57BL/6 mouse were separated by Matrigel method, and then cultured. Then, $1 \times 10^5$ cells were inoculated in a 24-well culture dish, and then treated with TNFα to induce VCAM-1 expression. Bone marrow-derived monocytes of GFP (green fluorescence protein) transgenic mouse were isolated using a magnetic bead specific to their surface marker CD11b, and $1 \times 10^6$ cells were treated to the vascular endothelial cells. After incubation for 30 min, unbound cells were removed by washing with PBS. 4% paraformaldehyde fixation was performed for 10 min, followed by PBS washing. Then, images of bound monocytes were obtained by fluorescence microscopy, and the number of cells was counted and analyzed by image analysis software.

As a result, approximately 20% reduction in the number of bound monocytes was observed in vascular endothelial cells treated with VCAM-1 antibody (7HT, 10 μg/ml), compared to those treated with control antibody (4BT, 10 μg/ml) (FIG. 9).

14. Analysis of Inhibitory Effect of VCAM-1 Antibody on Inflammatory Cell Trans-Migration Via in Vitro Transmigration Assay To confirm whether VCAM-1 antibody binds to vascular endothelial cells to inhibit transmigration of inflammatory cells, arterial vascular endothelial cells of C57BL/6 mouse were separated by Matrigel method, and cultured. Then, $5 \times 10^4$ cells were inoculated in the upper chamber of transwell, and then treated with TNFα to induce VCAM-1 expression. Bone marrow cells of mouse were separated, and $1 \times 10^5$ cells were treated to vascular endothelial cells, and the number of cells that transmigrated to the lower chamber was counted after 4 hrs and 18 hrs. As a result, when the number of cells were counted after 4 hrs, approximately 25% reduction was observed in the group treated with VCAM-1 antibody (7HT, 10 μg/ml), compared to that treated with control antibody (4BT, 10 μg/ml), and approximately 29% reduction was observed after 18 hrs (FIG. 10).

15. En Face Confocal Microscopy Assay for in Vivo Binding Test of VCAM-1 Ab (7HT)

To test the effect of VCAM-1 antibody as a therapeutic agent for cardiovascular diseases, experimental groups were divided into four groups of PBS, control antibody (4BT, 10 mg/kg), VCAM-1 antibody (7HT, 1 mg/kg), and VCAM-1 antibody (7HT, 10 mg/kg) in order to confirm whether VCAM-1 antibody specifically binds to VCAM-1-expressing arterial vascular endothelial cells when injected into mouse. Intraperitoneal injection was performed four times for 2 weeks, together with high-fat diet, and then the artery of each mouse was recovered, and reacted with Alexa 594-labelled anti-human IgG secondary antibody. To re-confirm the VCAM-1 expression of vascular endothelial cells, the artery was reacted with goat anti-mVCAM-1 antibody and Alexa 488-labelled anti-goat IgG secondary antibody. Then, the sections of arteries were visualized by confocal microscopy. As a result, VCAM-1 expression was clearly observed in the artery of each mouse, and a strong binding of VCAM-1 Ab was only observed in the mouse injected with a high dose of VCAM-1 Ab (7HT, 10 mg/kg) (FIG. 11).

16. Measurement of Changes in Body Weight and Feed Consumption

To measure changes in feed consumption and body weight by Ab treatment for 12 weeks, individual body weight and feed consumption of each group were measured once a week. As a result, there was no difference in the body weight between Groups 2-4 fed with a high-fat diet, except Group 1 fed with a normal chow diet. There was also no significant difference in feed consumption (FIG. 12).

17. Result of Hematologic Analysis

To separate the blood from animals of each experimental group, the blood was collected in a heparin-treated tube, and centrifuged at 13,000 rpm for 15 min. The total cholesterol (CHL), triglyceride (TG), high density lipoprotein (HDL), and low density lipoprotein (LDL) levels in blood were determined using an automatic biochemical analyzer (Hitachi 7150, Japan).

TABLE 2

| Mouse No. | | Material and Concentration | |
| --- | --- | --- | --- |
| Group 1 | 5 | Normal chow diet | PBS |
| Group 2 | 15 | HF (western) diet | Control group (4BT, 10 mg/kg) |
| Group 3 | 15 | HF (western) diet | VCAM-1 Low Dose (7HT, 1 mg/kg) |
| Group 4 | 15 | HF (western) diet | VCAM-1 High Dose (7HT, 10 mg/kg) |

Figure 13:
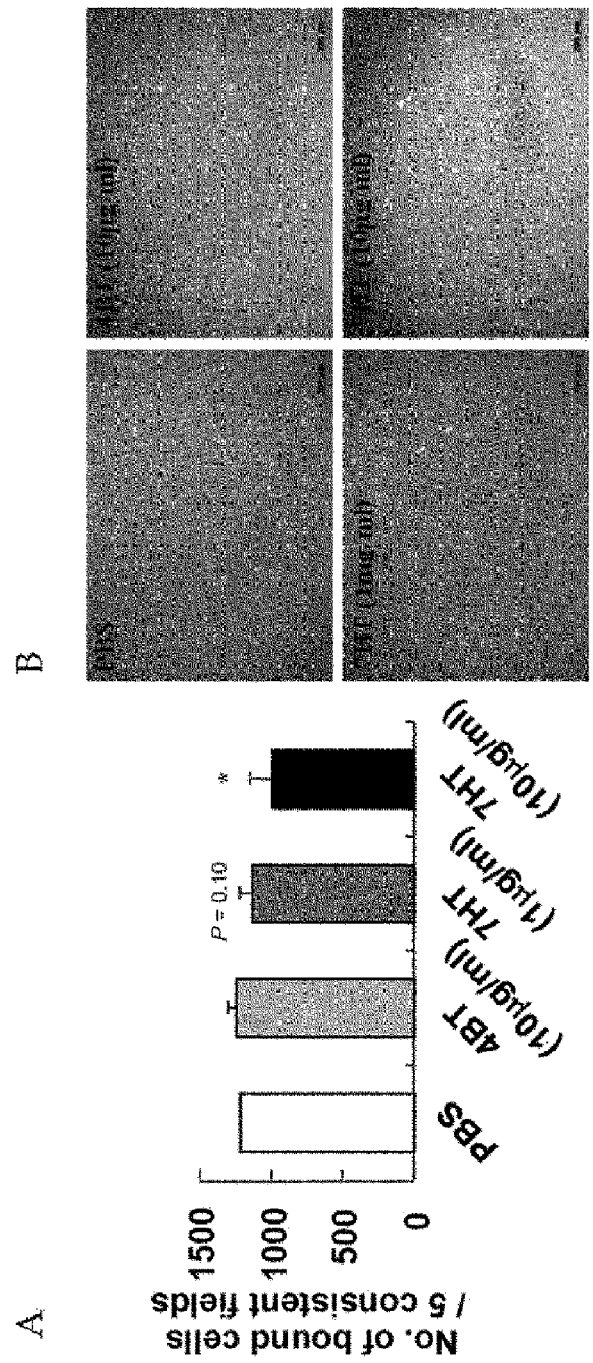
FIG. 13 is the result of analyzing inhibitory effect of VCAM-1 Ab on inflammatory cell adhesion by in vitro adhesion assay according to one embodiment of the present invention, in which (A) shows a graph of the number of bound monocytes, and (B) shows representative photographs.

It was found that the average and standard deviation of total cholesterol (T-CHO) in Group 1 treated with normal chow and PBS (phosphate buffered saline) was 615.20±61.67 (mg/dl) as the lowest level, the average and standard deviation of total cholesterol (T-CHO) in Group 2 treated with high-fat diet and 4BT Ab (10 mg/kg) was 1380.00±237.03 (mg/dl), the average and standard deviation of total cholesterol (T-CHO) in Group 3 treated with high-fat diet and 7HT Ab (1 mg/kg) was 1367.20±143.68 (mg/dl), and the average and standard deviation of total cholesterol (T-CHO) in Group 4 treated with high-fat diet and 7HT Ab (10 mg/kg) was 1323.60±209.38 (mg/dl). Compared to the control group (Group 2), there was no significant difference in the reduction of total cholesterol, and also in the reduction in HDL- and LDL-cholesterol, suggesting no effect of 7HT Ab injection on cholesterol metabolism/excretion. However, a reduction in triglyceride and glucose levels was observed in Group 4, and there was no difference in GOT, GPT and ALB levels for liver toxicity test (FIG. 13).

18. Formation of Atherosclerotic Plaque in the Aortic Arch and Size Measurement Thereof.

ApoE -/- mouse fed with high-fat diet (fat 20%, cholesterol 0.15%) for 12 weeks was sacrificed, and the heart and area from the ascending aorta to the thoracic aorta were dissected, and fixed in formalin. Then, the heart was trimmed, and embedded in OCT compound, and frozen in a deep freezer. The aortic arch was sectioned using a cryostat to a thickness of 6 to prepare slide. For fat staining, the slide was immersed in distilled water, and in absolute propylene glycol for 1 min, and then stained in an Oil-red solution for 16 hrs. Subsequently, the slide was immersed in 85% propylene glycol for 2 min, and washed with distilled water, and then mounted with aqueous mounting medium, followed by observation under an optical microscope. To measure the area of atherosclerotic plaque, each tissue was photographed, and then the area was measured and compared using an image measure soft ware (Axio Vision, Carl Zeiss).

It was found that the average and standard deviation of the lesion area in Group 1 treated with normal chow and PBS (phosphate buffered saline) was 88.55±21.65 (103 µm2) as the lowest value, the average and standard deviation of the lesion area in Group 2 treated with high-fat diet and 4BT Ab (10 mg/kg) was 345.20±74.03 (13 µm2) as the highest value, the average and standard deviation of the lesion area in Group 3 treated with high-fat diet and 7HT Ab (1 mg/kg) was 323.68±86.02 (103 µm2), and the average and standard deviation of the lesion area in Group 4 treated with high-fat diet and 7HT Ab (10 mg/kg) was 294.78±2.62 (103 µm2), suggesting a reduction in the area size, compared to the control group (Group 2) (FIG. 14).

19. Analysis of Atherosclerotic Plaque Formed in the Artery by En Face Method

A dissection was performed from the heart to the femoral artery, and then the surrounding fat tissue and adventitia area were completely removed, and the artery in the cardiac base was dissected, and separated from the heart. The artery was incised using a microscissors and microforceps, opened to expose the inside of the artery, and fixed with pins. The artery was fixed in 10% neutral buffered formalin solution for 16 hrs, and immersed in absolute propylene glycol for 1 min, and then stained in an Oil-red solution for 16 hrs. Subsequently, the sample was immersed in 85% propylene glycol for 2 min, and washed with distilled water. A stereoscopic microscope (Leica) was used to obtain images, and then the percentage of lesion to total arterial area was measured using an AxioVision AC imaging software.

Figure 16:
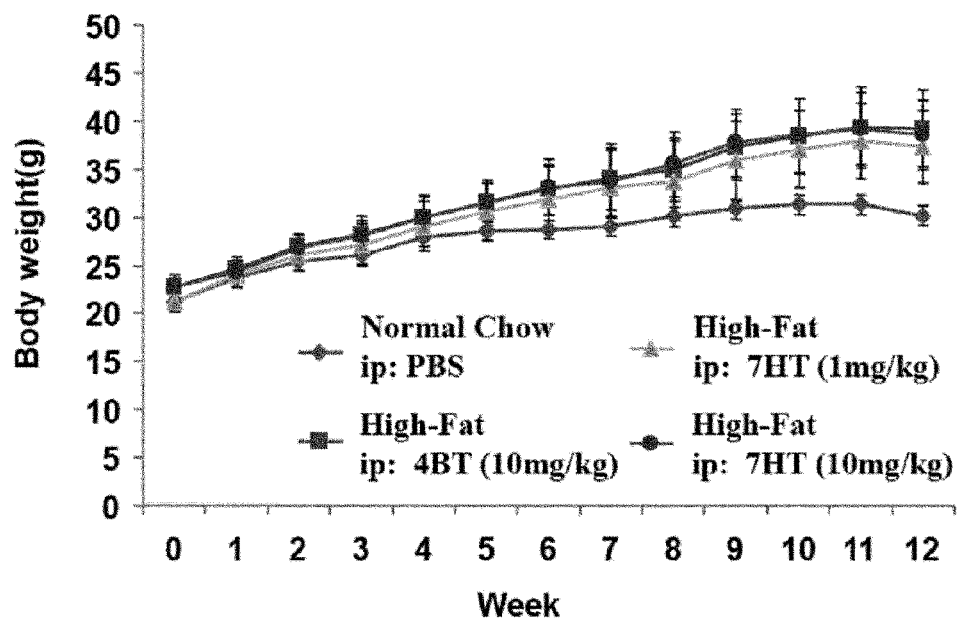
FIG. 16 is the result of measuring changes in the body weight and feed consumption of mouse according to one embodiment of the present invention.

It was found that the average and standard deviation of the lesion area in Group 1 treated with normal chow and PBS (phosphate buffered saline) was 1.75±0.47(%) as the lowest value, the average and standard deviation of the lesion area in Group 2 treated with high-fat diet and 4BT Ab (10 mg/kg) was 8.01±4.25(%) as the highest value, the average and standard deviation of the lesion area in Group 3 treated with high-fat diet and 7HT Ab (1 mg/kg) was 7.02±3.64(%), and the average and standard deviation of the lesion area in Group 4 treated with high-fat diet and 7HT Ab (10 mg/kg) was 5.43±1.61 (103 µm2), suggesting a significant reduction (P<0.05), compared to the control group (Group 2) (FIGS. 15 and 16).

20. Pathological Analysis of Main Organs for Toxicity Test of VCAM-1 Antibody

To examine toxicity of intraperitoneal injection of the antibody, the liver, kidney and spleen of each group were fixed in 10% formaldehyde to prepare paraffin blocks, and tissue sections were obtained using a microtome. The nucleus and cytoplasm were stained with hematoxylin & Eosin, and observed. As a result, no toxic phenotype such as inflammatory cell infiltration or tissue necrosis was observed, except fatty liver due to the high-fat diet (FIG. 17).

The invention claimed is:

1. A human recombinant monoclonal antibody, which specifically binds to human Vascular Cell Adhesion Molecule-1 (VCAM-1) to inhibit adhesion between leukocytes and activated endothelial cells and transmigration of leukocytes through the activated endothelial cells, wherein the human recombinant monoclonal antibody comprises:
   (a) a heavy chain variable region that contains heavy chain CDR1 as defined by SEQ ID NO.2; heavy chain CDR2 as defined by SEQ ID NO.3; and heavy chain CDR3 as defined by SEQ ID NO.4, and a light chain variable region that contains light chain CDR1 as defined by SEQ ID NO. 6; light chain CDR2 as defined by SEQ ID NO.7; and light chain CDR3 as defined by SEQ ID NO.8; or
   (b) a heavy chain variable region that contains heavy chain CDR1 as defined by SEQ ID NO. 10; heavy chain CDR2 as defined by SEQ ID NO. 11; and heavy chain CDR3 as defined by SEQ ID NO. 12, and a light chain variable region that contains light chain CDR1 as defined by SEQ ID NO. 14; light chain CDR2 as defined by SEQ ID NO. 15; and light chain CDR3 as defined by SEQ ID NO. 16.

2. The human recombinant monoclonal antibody according to claim 1, wherein the human recombinant monoclonal antibody binds to domain 1 or 2 of human Vascular Cell Adhesion Molecule-1 (VCAM-1).

3. The human recombinant monoclonal antibody according to claim 1, wherein the human recombinant monoclonal antibody of (a) comprises the heavy chain amino acid sequence as defined by SEQ ID NO.1.

4. The human recombinant monoclonal antibody according to claim 1, wherein the human recombinant monoclonal antibody of (a) comprises the light chain amino acid sequence as defined by SEQ ID NO. 5.

5. The human recombinant monoclonal antibody according to claim 1, wherein an association/dissociation constant (KD value) of the human recombinant monoclonal antibody to human VCAM-1 antigen is $0.1 \times 10^{-9}$ M to $7.0 \times 10^{-9}$ M.

6. The human recombinant monoclonal antibody according to claim 1, wherein the human recombinant monoclonal antibody of (b) comprises the heavy chain amino acid sequence as defined by SEQ ID NO. 9.

7. The human recombinant monoclonal antibody according to claim 1, wherein the human recombinant monoclonal antibody of (b) comprises the light chain amino acid sequence as defined by SEQ ID NO. 13.

8. A method for detecting VCAM-1 in a biological sample from a subject suspected of having inflammatory disease, cardiovascular disease or cancer, comprising:
   a) contacting the sample with the human recombinant monoclonal antibody of claim 1 and
   b) detecting an antigen-antibody reaction between the human recombinant monoclonal antibody of claim 1 and VCAM-1 in the biological sample.

9. The method according to claim 8, wherein the inflammatory disease is selected from the group consisting of asthma, diabetes, uveitis, ankylosing spondylitis, sepsis, endotoxin shock, hemodynamic shock, sepsis syndrome, ischemic reperfusion injury, malaria infection, mycobacterial infection, meningitis, psoriasis, congestive heart failure, fibrotic diseases, cachexia, transplant rejection, autoimmune diseases, AIDS-related opportunistic infection, arthritis, rheumatoid spondylitis, gout, ankylosing gout, Crohn's disease, ulcerative trigonitis, multiple sclerosis, erythema nodosum leprosum (ENL), radiation injury, hyperoxia-induced alveolar damage, and intestinal diseases.

10. The method according to claim 8, wherein the cardiovascular disease is selected from the group consisting of myocardial infarction, heart attack, stroke, arrhythmia, hypertension, hyperlipemia and arteriosclerosis.

11. A method of inhibiting adhesion between leukocytes and activated endothelial cells and transmigration of leukocytes through the activated endothelial cells, the method comprising contacting the leukocytes or activated endothelial cells with the human recombinant monoclonal antibody of claim 1.

12. A composition comprising the human recombinant monoclonal antibody of claim 1.

13. A therapeutic composition for inflammatory disease, cardiovascular disease or cancer, comprising the human recombinant monoclonal antibody of claim 1 and a pharmaceutically acceptable carrier.

14. The composition according to claim 13, wherein the inflammatory disease is selected from the group consisting of asthma, diabetes, uveitis, anklosing spondylitis, sepsis, endotoxin shock, hemodynamic shock, sepsis syndrome, ischemic reperfusion injury, malaria infection, mycobacterial infection, meningitis, psoriasis, congestive heart failure, fibrotic diseases cachexia, transplant rejection, autoimmune diseases, AIDS-related opportunistic infection, arthritis, rheumatoid spondylitis, gout, ankylosing gout, Crohn's disease, ulcerative trigonitis, multiple sclerosis, erythema nodosum leprosum (ENL), radiation injury, hyperoxia-induced alveolar damage, and intestinal diseases.

15. The composition according to claim 13, wherein the cardiovascular disease is selected from the group consisting of myocardial infarction, heart attack, stroke, arrhythmia, hypertension, hyperlipemia and arteriosclerosis.

16. A method for inhibiting adhesion between leukocytes and activated endothelial cells in a subject having an inflammatory disease, cardiovascular disease or cancer, the method comprising the step of administering the composition of claim 13 to the subject.

17. The method according to claim 16, wherein the inflammatory disease is selected from the group consisting of asthma, diabetes, uveitis, ankylosing spondylitis, sepsis, endotoxin shock, hemodynamic shock, sepsis syndrome, ischemic reperfusion injury, malaria infection, mycobacterial infection, meningitis, psoriasis, congestive heart failure, fibrotic diseases, cachexia, transplant rejection, autoimmune diseases, AIDS-related opportunistic infection, arthritis, rheumatoid spondylitis, gout, ankylosing gout, Crohn's disease, ulcerative trigonitis, multiple sclerosis, erythema nodosum leprosum (ENL), radiation injury, hyperoxia-induced alveolar damage, and intestinal diseases.

18. The method according to claim 16, wherein the cardiovascular disease is selected from the group consisting of myocardial infarction, heart attack, stroke, arrhythmia, hypertension, hyperlipemia and arteriosclerosis.

19. The human recombinant monoclonal antibody of claim 1, wherein the antibody is an antigen binding fragment that specifically binds to VCAM-1.

20. The human recombinant monoclonal antibody of claim 17, wherein the antigen binding fragment is selected from the group consisting of Fab' fragment, F(ab')$_2$ fragment, Fab fragment, Fv fragment, rIgG fragment, or recombinant single chain Fv fragment (scFv).

21. The method according to claim 8, wherein the cancer is selected from the group consisting of brain and spinal tumors, head and neck cancer, lung cancer, breast cancer, thymoma, mesothelioma, esophageal cancer, stomach cancer, colon cancer, liver cancer, pancreatic cancer, gallbladder cancer, renal cancer, prostate cancer, testicular cancer, germ cell tumor, ovarian cancer, cervical cancer, endometrial cancer, lymphoma, acute leukemia, chronic leukemia, multiple myeloma, sarcoma, malignant melanoma, and skin cancer.

22. The composition according to claim 13, wherein the cancer is selected from the group consisting of brain and spinal tumors, head and neck cancer, lung cancer, breast cancer, thymoma, mesothelioma, esophageal cancer, stomach cancer, colon cancer, liver cancer, pancreatic cancer, gallbladder cancer, renal cancer, prostate cancer, testicular cancer, germ cell tumor, ovarian cancer, cervical cancer, endometrial cancer, lymphoma, acute leukemia, chronic leukemia, multiple myeloma, sarcoma, malignant melanoma, and skin cancer.

23. The method according to claim 16, wherein the cancer is selected from the group consisting of brain and spinal tumors, head and neck cancer, lung cancer, breast cancer, thymoma, mesothelioma, esophageal cancer, stomach cancer, colon cancer, liver cancer, pancreatic cancer, gallbladder cancer, renal cancer, prostate cancer, testicular cancer, germ cell tumor, ovarian cancer, cervical cancer, endometrial cancer, lymphoma, acute leukemia, chronic leukemia, multiple myeloma, sarcoma, malignant melanoma, and skin cancer.

* * * * *

SEQUENCE LISTING

```
<160> NUMBER OF SEQ ID NOS: 29

<210> SEQ ID NO 1
<211> LENGTH: 121
<212> TYPE: PRT
<213> ORGANISM: Artificial Sequence
<220> FEATURE:
<223> OTHER INFORMATION: Synthetic: 6H heavy chain variable region

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Gly Ile Ser Tyr Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                    85                  90                  95

Ala Lys Gly Pro Phe Arg Met Arg Phe Arg Ser Phe Asp Tyr Trp Gly
                100                 105                 110

Gln Gly Thr Leu Val Thr Val Ser Ser
            115                 120

<210> SEQ ID NO 2
<211> LENGTH: 6
<212> TYPE: PRT
<213> ORGANISM: Artificial Sequence
<220> FEATURE:
<223> OTHER INFORMATION: Synthetic: 6H CDR1 of a heavy chain variable
      region

<400> SEQUENCE: 2

Ser Ser Tyr Asp Met Ser
1               5

<210> SEQ ID NO 3
<211> LENGTH: 17
<212> TYPE: PRT
<213> ORGANISM: Artificial Sequence
<220> FEATURE:
<223> OTHER INFORMATION: Synthetic: 6H CDR2 of a heavy chain variable
      region

<400> SEQUENCE: 3

Gly Ile Ser Tyr Ser Gly Gly Ser Thr Tyr Tyr Ala Asp Ser Val Lys
1               5                   10                  15

Gly

<210> SEQ ID NO 4
<211> LENGTH: 12
<212> TYPE: PRT
<213> ORGANISM: Artificial Sequence
<220> FEATURE:
<223> OTHER INFORMATION: Synthetic: 6H CDR3 of a heavy chain variable
      region

<400> SEQUENCE: 4

Gly Pro Phe Arg Met Arg Phe Arg Ser Phe Asp Tyr
1               5                   10

<210> SEQ ID NO 5
<211> LENGTH: 110
<212> TYPE: PRT
<213> ORGANISM: Artificial Sequence
<220> FEATURE:
<223> OTHER INFORMATION: Synthetic: 6H light chain variable region

<400> SEQUENCE: 5

Gln Ser Val Leu Thr Gln Pro Pro Ser Ala Ser Gly Thr Pro Gly Gln
1               5                   10                  15

Arg Ala Thr Ile Ser Cys Thr Gly Ser Ser Ser Asn Ile Gly Ser Asn
                20                  25                  30

Ser Val Ser Trp Tyr Gln Gln Leu Pro Gly Thr Ala Pro Lys Leu Leu
            35                  40                  45

Ile Tyr Ala Asn Ser Asn Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80
```

```
Ser Glu Asp Glu Ala Asp Tyr Tyr Cys Gly Thr Trp Asp Ala Ser Leu
                85                  90                  95

Ser Ala Tyr Val Phe Gly Gly Gly Thr Lys Leu Thr Val Leu
            100                 105                 110

<210> SEQ ID NO 6
<211> LENGTH: 13
<212> TYPE: PRT
<213> ORGANISM: Artificial Sequence
<220> FEATURE:
<223> OTHER INFORMATION: Synthetic: CDR1 of a light chain variable
      region

<400> SEQUENCE: 6

Thr Gly Ser Ser Ser Asn Ile Gly Ser Asn Ser Val Ser
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic: 6H CDR2 of a light chain variable
      region

<400> SEQUENCE: 7

Ala Asn Ser Asn Arg Pro Ser
1               5

<210> SEQ ID NO 8
<211> LENGTH: 11
<212> TYPE: PRT
<213> ORGANISM: Artificial Sequence
<220> FEATURE:
<223> OTHER INFORMATION: Synthetic: 6H CDR3 of a light chain variable
      region

<400> SEQUENCE: 8

Gly Thr Trp Asp Ala Ser Leu Ser Ala Tyr Val
1               5                   10

<210> SEQ ID NO 9
<211> LENGTH: 327
<212> TYPE: PRT
<213> ORGANISM: Artificial Sequence
<220> FEATURE:
<223> OTHER INFORMATION: Synthetic: 7HT heavy chain variable region

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
```

```
                    115                 120                 125
Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 10
<211> LENGTH: 10
<212> TYPE: PRT
<213> ORGANISM: Artificial Sequence
<220> FEATURE:
<223> OTHER INFORMATION: Synthetic: 7HT CDR1 of heavy chain variable
      region

<400> SEQUENCE: 10

Gly Phe Thr Phe Asn Asp Ala Trp Met Thr
1               5                   10

<210> SEQ ID NO 11
<211> LENGTH: 19
<212> TYPE: PRT
<213> ORGANISM: Artificial Sequence
<220> FEATURE:
<223> OTHER INFORMATION: Synthetic: 7HT CDR2 of heavy chain variable
      region

<400> SEQUENCE: 11

Arg Ile Lys Ser Thr Thr Asp Gly Gly Thr Thr Asn Tyr Ala Ala Pro
1               5                   10                  15

Val Glu Gly

<210> SEQ ID NO 12
<211> LENGTH: 17
<212> TYPE: PRT
<213> ORGANISM: Artificial Sequence
<220> FEATURE:
<223> OTHER INFORMATION: Synthetic: 7HT CDR3 of heavy chain variable
      region
```

```
<400> SEQUENCE: 12

Ile Pro Leu Phe Asn His Asp Ser Gly Gly Tyr His Gly Ala Phe Asp
1               5                   10                  15

Ile

<210> SEQ ID NO 13
<211> LENGTH: 106
<212> TYPE: PRT
<213> ORGANISM: Artificial Sequence
<220> FEATURE:
<223> OTHER INFORMATION: Synthetic: 7HT light chain variable region

<400> SEQUENCE: 13

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 14
<211> LENGTH: 17
<212> TYPE: PRT
<213> ORGANISM: Artificial Sequence
<220> FEATURE:
<223> OTHER INFORMATION: Synthetic: 7HT CDR1 of light chain variable
      region

<400> SEQUENCE: 14

Lys Ser Ser Gln Ser Val Leu Tyr Ser Ser Asn Asn Lys Asn Tyr Leu
1               5                   10                  15

Ala

<210> SEQ ID NO 15
<211> LENGTH: 7
<212> TYPE: PRT
<213> ORGANISM: Artificial Sequence
<220> FEATURE:
<223> OTHER INFORMATION: Synthetic: 7HT CDR2 of light chain variable
      region

<400> SEQUENCE: 15

Trp Ala Ser Thr Arg Glu Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic: 7HT CDR3 of light chain variable region

<400> SEQUENCE: 16

Gln Glu Ser Tyr Ser Ala Pro Tyr Thr
1               5
```

```
<210> SEQ ID NO 17
<211> LENGTH: 38
<212> TYPE: DNA
<213> ORGANISM: Artificial Sequence
<220> FEATURE:
<223> OTHER INFORMATION: Synthetic forward primer of 1-2 domain of VCAM-
      1

<400> SEQUENCE: 17 caggggggccg tgggggccctt taaaatcgag accacccc                                38

<210> SEQ ID NO 18
<211> LENGTH: 40
<212> TYPE: DNA
<213> ORGANISM: Artificial Sequence
<220> FEATURE:
<223> OTHER INFORMATION: Synthetic reverse primer of 1-2 domain of VCAM-
      1

<400> SEQUENCE: 18
tagcggccga cgcggccaat tgcaattctt ttacagcctg                                40

<210> SEQ ID NO 19
<211> LENGTH: 38
<212> TYPE: DNA
<213> ORGANISM: Artificial Sequence
<220> FEATURE:
<223> OTHER INFORMATION: Synthetic forward primer of 1-4 domain of VCAM-
      1

<400> SEQUENCE: 19 caggggggccg tggggggcctt taaaatcgag accacccc                                38

<210> SEQ ID NO 20
<211> LENGTH: 39
<212> TYPE: DNA
<213> ORGANISM: Artificial Sequence
<220> FEATURE:
<223> OTHER INFORMATION: Synthetic reverse primer of 1-4 domain of VCAM-
      1

<400> SEQUENCE: 20
tagcggccga cgcggccaag agctccacct ggattccct                                 39

<210> SEQ ID NO 21
<211> LENGTH: 25
<212> TYPE: PRT
<213> ORGANISM: Artificial Sequence
<220> FEATURE:
<223> OTHER INFORMATION: Synthetic peptide

<400> SEQUENCE: 21

Glu Val Gln Leu Val Gln Ser Gly Gly Asp Leu Val Lys Pro Gly Glu
1               5                   10                  15

Ser Leu Arg Leu Ser Cys Ala Ala Ser
            20                  25

<210> SEQ ID NO 22
<211> LENGTH: 14
<212> TYPE: PRT
<213> ORGANISM: Artificial Sequence
<220> FEATURE:
<223> OTHER INFORMATION: Synthetic peptide

<400> SEQUENCE: 22

Trp Val Arg Gln Pro Pro Gly Lys Gly Leu Glu Trp Val Gly
```

```
<210> SEQ ID NO 23
<211> LENGTH: 32
<212> TYPE: PRT
<213> ORGANISM: Artificial Sequence
<220> FEATURE:
<223> OTHER INFORMATION: Synthetic peptide

<400> SEQUENCE: 23

Arg Phe Thr Ile Ser Arg Asp Asp Ser Lys Asn Thr Leu Tyr Leu Glu
1               5                   10                  15

Met Asn Ser Leu Arg Ala Glu Asp Thr Ala Val Tyr Tyr Cys Ala Arg
            20                  25                  30

<210> SEQ ID NO 24
<211> LENGTH: 11
<212> TYPE: PRT
<213> ORGANISM: Artificial Sequence
<220> FEATURE:
<223> OTHER INFORMATION: Synthetic peptide

<400> SEQUENCE: 24

Trp Gly Gln Gly Thr Met Val Thr Val Ser Ser
1               5                   10

<210> SEQ ID NO 25
<211> LENGTH: 23
<212> TYPE: PRT
<213> ORGANISM: Artificial Sequence
<220> FEATURE:
<223> OTHER INFORMATION: Synthetic peptide

<400> SEQUENCE: 25

Asp Ile Gln Met Thr Gln Ser Pro Ser Ser Leu Ala Val Ser Leu Gly
1               5                   10                  15

Glu Arg Ala Thr Ile Asn Cys
            20

<210> SEQ ID NO 26
<211> LENGTH: 15
<212> TYPE: PRT
<213> ORGANISM: Artificial Sequence
<220> FEATURE:
<223> OTHER INFORMATION: Synthetic peptide

<400> SEQUENCE: 26

Trp Tyr Gln Gln Lys Pro Gly Gln Pro Pro Lys Leu Leu Ile Tyr
1               5                   10                  15

<210> SEQ ID NO 27
<211> LENGTH: 32
<212> TYPE: PRT
<213> ORGANISM: Artificial Sequence
<220> FEATURE:
<223> OTHER INFORMATION: Synthetic peptide

<400> SEQUENCE: 27

Gly Val Pro Asp Arg Phe Ser Gly Ser Gly Ser Gly Thr Asp Phe Thr
1               5                   10                  15

Leu Thr Ile Ser Ser Leu Gln Pro Glu Asp Phe Ala Ser Tyr Tyr Cys
            20                  25                  30

<210> SEQ ID NO 28
<211> LENGTH: 11
<212> TYPE: PRT
```

```
<213> ORGANISM: Artificial Sequence
<220> FEATURE:
<223> OTHER INFORMATION: Synthetic peptide

<400> SEQUENCE: 28

Phe Gly Gln Gly Thr Lys Val Glu Ile Lys Arg
1               5                   10

<210> SEQ ID NO 29
<211> LENGTH: 18
<212> TYPE: DNA
<213> ORGANISM: Artificial Sequence
<220> FEATURE:
<223> OTHER INFORMATION: Synthetic primer

<400> SEQUENCE: 29
aaatgggcgg taggcgtg                                                 18
```